(12) United States Patent
Bialer et al.

(10) Patent No.: US 8,518,979 B2
(45) Date of Patent: Aug. 27, 2013

(54) ALPHA-HALO- AND ALPHA-ALKYL-CYCLOPROPYLCARBOXY COMPOUNDS AND USES THEREOF

(75) Inventors: Meir Bialer, Jerusalem (IL); Boris Yagen, Jerusalem (IL); Neta Pessah, Tel Aviv (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 491 days.

(21) Appl. No.: 12/527,707

(22) PCT Filed: Feb. 19, 2008

(86) PCT No.: PCT/IL2008/000217
§ 371 (c)(1),
(2), (4) Date: Feb. 12, 2010

(87) PCT Pub. No.: WO2008/102348
PCT Pub. Date: Aug. 28, 2008

(65) Prior Publication Data
US 2010/0152254 A1    Jun. 17, 2010

Related U.S. Application Data

(60) Provisional application No. 60/902,385, filed on Feb. 21, 2007.

(51) Int. Cl.
*A61K 31/433* (2006.01)
*A61K 31/17* (2006.01)
*A61K 31/164* (2006.01)
*C07D 285/135* (2006.01)
*C07C 275/18* (2006.01)
*C07C 233/61* (2006.01)
*C07C 233/58* (2006.01)

(52) U.S. Cl.
USPC ........... 514/363; 514/594; 514/616; 514/624; 548/139; 564/45; 564/152; 564/190

(58) Field of Classification Search
None
See application file for complete search history.

(56) References Cited

U.S. PATENT DOCUMENTS 4,003,945 A    1/1977    Kitamura et al.

FOREIGN PATENT DOCUMENTS

| JP | 08-245594 | 9/1996 |
| WO | WO 03/064374 | 8/2003 |
| WO | WO 2004/076432 | 9/2004 |
| WO | WO 2008/063625 | * 5/2008 |
| WO | WO 2008/102348 | 8/2008 |

OTHER PUBLICATIONS

Hitchcock et al. J. Chem. Soc., Perkin Trank. 1, 1998, pp. 3181-3206.*
"Guidance for Industry: Q3C—Tables and List." US DHHS, FDA, CDER, CBER, Nov. 2003. Revision 1.*
Pessah et al. "α-Fluoro-2,2,3,3-Tetramethylcyclopropanecarboxamide, A Novel Potent Anticonvulsant Derivative of a Cyclic Analogue of Valproic Acid", Journal of Medicinal Chemistry, 52: 2233-2242, 2009.
Response Dated Oct. 7, 2010 to Communication Pursuant to Article 94(3) EPC of Dec. 23, 2009 From the European Patent Office Re.: Application No. 08710217.4.
Pessah et al. "Comparative Pharmacodynamic and Pharmacokinetic Analysis of Two Anticonvulsant Halo Derivatives of 2,2,3,3-Tetramethylcyclopropanecarboxamide, An Amide of a Cyclic Analog of Valproic Acid", Epilepsoa, 51(10): 1944-1953, 2010.
Communication Pursuant to Article 94(3) EPC Dated Sep. 23, 2011 From the European Patent Office Re. : Application No. 08710217.4.
Bolton "1-Alkylcyclopropanecarboxylates: An Extension of Pyrethroid Structure-Activity Relationships", Pesticide Science, XP002482233, 7: 251-257, 1976. Compounds IV K, V K.
Isoherranen et al. "Anticonvulsant Profile and Teratogenicity of N-Methyl-Tetramethylcyclopropyl Carboxamide: A New Antiepileptic Drug", Epilepsia, XP001181906, 43(2): 115-126, Jan. 1, 2002. Compounds M-TMCD.
Isoherranen et al. "New CNS-Active Drugs Which Are Second-Generation Valproic Acid: Can They Lead to the Development of a Magic Bullet?", Current Opinion in Neurology, XP008035486, 16(2): 203-211, Jan. 1, 2003.
International Preliminary Report on Patentability Dated Aug. 26, 2009 From the International Bureau of WIPO Re.: Application No. PCT/IL2008/000217.
International Search Report Dated Jun. 17, 2008 From the International Searching Authority Re.: Application No. PCT/IL2008/000217.
Written Opinion Dated Jun. 17, 2008 From the International Searching Authority Re.: Application No. PCT/IL2008/000217.
Communication Pursuant to Article 94(3) EPC Dated Dec. 23, 2009 From the European Patent Office Re.: Application No. 08710217.4.
Office Action Dated Jun. 10, 2012 From the Israel Patent Office Re. Application No. 200459 and Its Translation Into English.
Office Action Dated May 8, 2013 From the Israel Patent Office Re. Application No. 200459 and Its Translation Into English.

* cited by examiner

*Primary Examiner* — Alicia L Otton

(57) ABSTRACT

Novel Alpha-halo- and Alpha-alkyl-cyclopropylcarboxy compounds, and uses of these and related compounds in the treatment of a variety of neurological diseases and disorders, and particularly epilepsy, are provided.

14 Claims, 1 Drawing Sheet

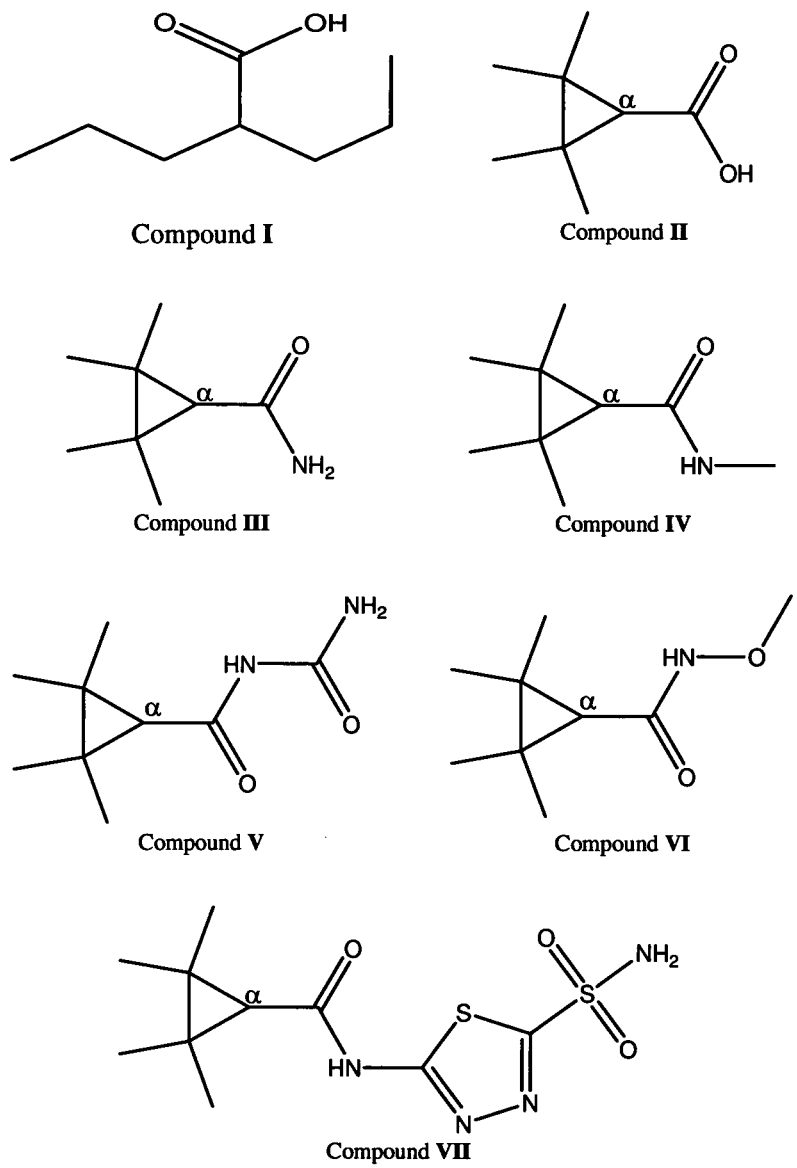

ALPHA-HALO- AND ALPHA-ALKYL-CYCLOPROPYLCARBOXY COMPOUNDS AND USES THEREOF

RELATED APPLICATIONS

This Application is a National Phase of PCT Patent Application No. PCT/IL2008/000217 having International filing date of Feb. 19, 2008, which claims the benefit of U.S. Provisional Patent Application No. 60/902,385 filed on Feb. 21, 2007. The contents of the above Applications are all incorporated herein by reference.

FIELD AND BACKGROUND OF THE INVENTION

The present invention relates to novel derivatives of cyclopropanecarboxylic acid, pharmaceutical compositions comprising same and uses thereof in a variety of therapeutic applications.

Epilepsy, also referred to as a seizure disorder, is a chronic disorder of the central nervous system (CNS), characterized either by recurrent and unprovoked episodic loss of attention or sleepiness or by severe convulsions with loss of consciousness called seizures or fits. The seizures are considered as transient symptoms which are attributed to irregular immoderate or coincident neuronal activity in the brain. This incurable yet typically therapeutically controlled medical condition affects about 0.5% of the population, whereas about 1.5-5.0% of the population may have a seizure in their lifetime at any age.

Prolonged seizures may lead to the development of Status epilepticus (SE), which is a life threatening cerebral state of a persistent seizure. SE can be defined broadly as one continuous seizure or a series of recurrent seizures wherein the subject does not regain consciousness between seizures for longer than 30 minutes. It is believed that 5 minutes are sufficient to cause irreparable damage to the neurons, and in SE cases seizures are unlikely to terminate spontaneously by that time. In a subject known to suffer from epilepsy, SE can be brought about or be aggravated by poor compliance to treatment (adherence to medication regimen), alcohol withdrawal and/or metabolic disturbances. As a primary presentation it may indicate a brain tumor or abscess. SE was also reported to be caused by various nerve agents (organophosphates) such as sarin, VX and soman.

The treatment of epilepsy typically consists of oral administration of anti-convulsants or antiepileptic drugs (AEDs). This symptomatic treatment is aimed at reducing the number and severity of future seizures. The efficacy of AEDs depends on the patient's response to any particular AED, which in turn is selected according to the type and severity of the seizure. Some epileptic patients are known to respond well to one AED and may respond poorly or even worsen the condition by others. When the epileptic condition seems not to respond to the use of AEDs, it is referred to as "refractory epilepsy", which is typically treated by brain surgery to remove the abnormal brain cells that are causing the seizures, or by a vagal nerve stimulator, which is implanted in the chest, which helps reducing the number of seizures.

Currently, four major AEDs are used for the treatment of epilepsy: phenytoin (marketed as Dilantin® in the USA and as Epanutin® in the UK); carbamazepine (sold under the brand-names Biston, Calepsin, Carbatrol, Epitol, Equetro, Finlepsin, Sirtal, Stazepine, Tegretol, Telesmin, Timonil); phenobarbital (also known as phenobarbitone or Luminal®) and valproic acid (VPA).

However, only about 75% of epileptic patients respond to the presently used AEDs. Furthermore, these widely used AEDs have been shown to cause some rare and severe adverse side effects such as teratogenicity that limit their use. Therefore, in a significant part of epileptic cases, and particularly when these AEDs are administered repetitively as the main treatment for chronic epileptic conditions, the adverse effects associated therewith upset the balance of beneficial-to-harmful effect, and leaves the patient with little or no salvation.

Status epilepticus is typically treated with benzodiazepines such as diazepam, clonazepam, lorazepam phenobarbital, phenytoin and lorazepam. Phenytoin and its prodrug fosphenytoin as well as other hydantoin derivatives are also used to treat SE, and are typically co-administered with a benzodiazepine phenobarbital or barbiturate. Barbiturates such as phenobarbital, secobarbital, thiopental or pentobarbital, are still used today to treat SE if benzodiazepines or the hydantoins are not an option, primarily by induction of a barbituric coma. In that respect of coma-causing agents, general anesthetics such as propofol and lidocaine are used where barbiturates are ineffective or cannot be used for some other reason.

Valproic acid (VPA, Compound I, see FIG. 1) is a broad-spectrum antiepileptic and CNS active agent and one of the abovementioned AEDs which is still in use as an anticonvulsant and mood-stabilizing drug in the treatment of epilepsy [1]. Valproic acid has also been used in the treatment of other CNS-related conditions such as bipolar disorder [1], neuropathic pain, myoclonus, schizophrenia and for migraine prophylaxis [2, 3].

VPA is believed to act through a combination of mechanisms: as a membrane stabilizer, via GABA transaminase inhibition which results in enhanced GABA signaling, and as a serotonergic inhibitor which reduces NMDA-receptor mediated glutamate excitation [5-7]. In principle, such multilevel action is highly advantageous, promising improved efficacy with reduced side effects. Nonetheless, the clinical use of VPA is severely limited by two rare, yet potentially life-threatening side effects, teratogenicity and hepatotoxicity, which restrict its utilization in women of child bearing age and in children. While VPA's teratogenicity is associated with the parent compound [8], its hepatotoxicity results from biotransformation into hepatotoxic metabolites with a terminal double bond, specifically 4-ene-VPA [9].

Extensive efforts have therefore been directed towards therapeutically active derivatives of VPA which exhibit improved activity and/or reduced side effects.

Therapeutically active derivatives of VPA include the salt sodium valproate which is used in anticonvulsant formulations, and valproate semisodium, which is used as an anticonvulsant and a mood stabilizer. A homologue of VPA wherein one of the alkyl chains is three carbons longer, arundic acid ((R)-(−)-2-propyloctanoic acid, also known as ONO-2506), is currently under clinical development for the potential treatment of stroke, as well as of other neurodegenerative diseases including amytrophic lateral sclerosis (ALS), Alzheimer's disease and Parkinson's disease [4].

A series of VPA-amide analogue and derivatives thereof was developed via a series of structure (pharmacokinetic/pharmacodynamic) activity relationship studies, and were found to exhibit improved anticonvulsant activity while avoiding teratogenicity and hepatotoxicity [10-13]. Some of these VPA amide derivatives were also active in animal models of neuropathic pain [14, 15] and bipolar disorder [16, 17].

2,2,3,3-Tetramethylcyclopropanecarboxylic acid (TMCA, Compound II, see FIG. 1) is a cyclic analog of VPA which was shown to possess weak anticonvulsant activity; however the toxic effect of TMCA overshadows its beneficial activity as an anticonvulsant [10, 14].

U.S. Patent Application having Publication No. 20060004098 teaches the use of various VPA-like and TMCA derivative compounds for treating neuropathic pain, migraine, psychiatric disorder and/or neuronal degeneration.

U.S. Pat. No. 5,880,157 discloses ester derivatives of TMCA as well as processes for preparing same and pharmaceutical preparations comprising the same, particularly intended for the treatment of epilepsy.

U.S. Patent Application having Publication No. 20050131069 teaches derivatives of N-hydroxyalkyl-tetramethylcyclopropane carboxamide, pharmaceutical compositions containing same, methods for their preparation, and use thereof for the treatment of epilepsy, neurological, affective and psychotic disorders and for the treatment of pain and migraine.

U.S. Patent Application having Publication No. 20060148861 teaches derivatives of 2,2,3,3-tetramethylcyclopropane carboxamide, pharmaceutical compositions containing same and uses thereof for treating psychotic disorders, neurodegenerative diseases, epilepsy and pain. According to the teachings of this patent application, the corresponding amide of TMCA, 2,2,3,3-tetramethylcyclopropanecarboxamide (Compound III, see FIG. 1) and its N-methyl derivative N-methyl-2,2,3,3-tetramethylcyclopropanecarboxamide (Compound IV, see FIG. 1) were found to possess a broad spectrum anticonvulsant activity while not evoking teratogenic and probably hepatotoxic effects [10, 11]. In following studies, 2,2,3,3-tetramethylcyclopropylcarbonyl urea (Compound V, see FIG. 1) was found to be the most promising compound, having a protective index, namely $TD_{50}$-to-$ED_{50}$ ratio of 18.5 in the maximal electroshock (MES) tests, compared to 1.6 measured for VPA [13].

Unlike VPA, TMCA (Compound II) and the tetramethylcyclopropyl amide analogues of VPA, namely Compounds III, IV and V, possess two quaternary carbons at the β-position relative to the carbonyl and hence, as opposed to VPA, these derivatives cannot undergo bio-transformation into hepatotoxic metabolites with a terminal double bond [10-13]. These compounds were found more potent than VPA as therapeutics for neuropathic pain in spinal nerve ligated rat models [14]. The most promising analogue, Compound IV, was further found to be non-neurotoxic, non-sedative and equipotent to GABApentin (Neurontin®), a currently leading drug for neuropathic pain treatment.

U.S. Pat. No. 6,960,687 discloses derivatives of N-(hydroxy-substituted)-2,2,3,3-tetramethylcyclopropanecarboxamide, as well as pharmaceutical compositions containing same, methods for their preparation, and use thereof for the treatment of epilepsy, neurological, affective and psychotic disorders and for the treatment of pain and migraine.

The N-methoxy derivative of TMCA, N-methoxy-2,2,3,3-tetramethylcyclopropanecarboxamide (Compound VI, see FIG. 1) and the 1,3,4-thiadiazole-2-sulfonamide derivative of TMCA, N-(1,3,4-thiadiazole-2-sulfonamide)-2,2,3,3-tetramethylcyclopropanecarboxamide (Compound VII, see FIG. 1) were shown to possess promising anticonvulsant activity in the maximal electroshock (MES) and in the subcutaneous metrazol injected (scMet) induced seizure model in rats. In these studies, Compound VI exhibited $ED_{50}$ values of 57 mg/kg MES tests and 9.8 mg/kg in scMet tests, as measured in seizure model in rats injected intraperitoneally. This compound was found less teratogenic than VPA [Okada et al., *Birth Defect Research* (Part B) 77:227-233 (2006)]. Compound VII exhibited good MES-$ED_{50}$ values of 17 mg/kg in mice models injected intraperitoneally, and 9.2 mg/kg in orally treated rat models, and was found noneneurotoxic at 500 mg/kg doses. However, analysis in a mouse model for VPA-induced teratogenicity showed that Compound VII is teratogenic (unpublished results).

In recent studies comparing α-fluorinated and non-fluorinated VPA, it was shown that α-fluorination leads to a chemical structure with a greatly reduced adverse hepatotoxic activity [18, 19]. Other works, such as described in Hoffmann, H. M. R. et al., [*Ang. Chem.*, 1982, 94(1), 79-80]; and Wulff, J. M. et al., [*Ang. Chem.*, 1985, 97(7), 597-9]; report the preparation of a few α-bromo-derivatives of 2,2,3,3-tetramethylcyclopropane-carboxylic acid. Likhotvorik, I. et al., [*J. Am. Chem. Soc.* 2001, 123, 6061-6068]; Tippmann, E. M. et al., [*Org. Lett.*, 26(5), 2003]; Tippmann, E. M. et al., [*J. Am. Chem. Soc.*, 126(9), 18, 2004, 5751]; and Martinu, T. et al., [*J. Org. Chem.*, 2004, 69, 7359-7362], report the preparation of a few α-fluoro, α-bromo and α-chloro-derivatives of 2,2,3,3-tetramethylcyclopropane-carboxylic acid, yet the therapeutic activity thereof was neither described nor suggested and tested.

Hence, although massive studies have been conducted regarding therapeutically active VPA derivatives, efficacious derivatives which overcome the limitations associated with VPA therapy have not been uncovered yet. While 2,2,3,3-tetramethylcyclopropane carboxamides were found as promising candidates in this respect, a need still remains for derivatives thereof that would exhibit an improved effect.

There is thus a widely recognized need for, and it would be highly advantageous to have novel derivatives of cyclopropylcarboxy compounds, devoid of the above limitations.

SUMMARY OF THE INVENTION

The present inventors have now designed and successfully prepared and practiced novel classes of α-substituted cyclopropylcarboxy compounds, and more particularly, novel α-halo- and α-alkyl-substituted cyclopropylcarboxy compounds.

Thus, according to one aspect of the present invention there is provided a compound having the general Formula I:

Formula I an enantiomer, a prodrug, a hydrate, a solvate or a pharmaceutically acceptable salt thereof, wherein:

X is halide or an alkyl having from 1 to 20 carbon atoms;

$R_1$-$R_4$ are each independently an alkyl having from 1 to 20 carbon atoms;

Y is selected from the group consisting of $NR_5$, O and S;

A is selected from the group consisting of O, N and S; and $R_5$ is selected from the group consisting of hydrogen, alkyl and cycloalkyl; and $D_1$ and $D_2$ are each independently selected from the group consisting of hydrogen, alkyl, alkenyl, alkynyl, cycloalkyl, aryl, heteroaryl, halide, hydroxy, alkoxy, hydroxyalkyl, thiohydroxy, thioalkoxy, thiohydroxyalkyl, aryloxy, thioaryloxy, haloalkyl, amine, carbonyl, amide, thioamide, carbamate, urea, alkyl-sulfonamide, aryl-sulfonamide, alkyl-aryl-sulfonamide, thiadiazole-sulfonamide, alkyl-thiadiazole-sulfonamide or absent;

with the proviso that when X is halide, Y is O and A is N or O, one or more of $D_1$ and $D_2$ is selected from the group consisting of alkenyl, alkynyl, cycloalkyl, aryl, heteroaryl, hydroxy, alkoxy, hydroxyalkyl, thiohydroxy, thioalkoxy, thiohydroxyalkyl, aryloxy, thioaryloxy, haloalkyl, amine, carbonyl, amide, thioamide, carbamate, urea, alkyl-sulfonamide, aryl-sulfonamide, alkyl-aryl-sulfonamide, thiadiazole-sulfonamide, alkyl-thiadiazole-sulfonamide.

According to another aspect of the present invention there is provided a process of preparing the compound having the general Formula I hereinabove, the process is effected by reacting a compound having the general Formula II:

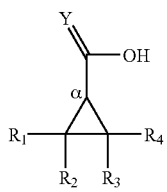

Formula II wherein:
$R_1$-$R_4$ are each independently an alkyl having from 1 to 20 carbon atoms;
Y is selected from the group consisting of $NR_5$, O and S; and
$R_5$ is selected from the group consisting of hydrogen, alkyl, alkenyl, alkynyl, and cycloalkyl;
with a halogenating agent or an alkylating agent, to thereby obtain a compound having the general Formula III:

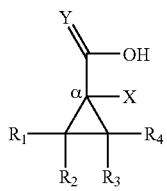

Formula III wherein:
X is halide or an alkyl having from 1 to 20 carbon atoms; and
reacting the compound having the general Formula III with a compound having the general Formula IV:

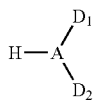

Formula IV wherein:
A is selected from the group consisting of O, N and S; and
$D_1$ and $D_2$ are each independently selected from the group consisting of hydrogen, alkyl, alkenyl, alkynyl, cycloalkyl, aryl, heteroaryl, halide, hydroxy, alkoxy, hydroxyalkyl, thiohydroxy, thioalkoxy, thiohydroxyalkyl, aryloxy, thioaryloxy, haloalkyl, amine, carbonyl, amide, thioamide, carbamate, urea, alkyl-sulfonamide, aryl-sulfonamide, alkyl-aryl-sulfonamide, thiadiazole-sulfonamide, alkyl-thiadiazole-sulfonamide or absent, with the proviso that when X is halide, Y is O and A is N or O, one or more of $D_1$ and $D_2$ is selected from the group consisting of alkenyl, alkynyl, cycloalkyl, aryl, heteroaryl, hydroxy, alkoxy, hydroxyalkyl, thiohydroxy, thioalkoxy, thiohydroxyalkyl, aryloxy, thioaryloxy, haloalkyl, amine, carbonyl, amide, thioamide, carbamate, urea, alkyl-sulfonamide, aryl-sulfonamide, alkyl-aryl-sulfonamide, thiadiazole-sulfonamide, alkyl-thiadiazole-sulfonamide.

According to further features in some embodiments of the invention described below, the halogenating agent is a N-halobenzenesulfonimide.

According to still further features in some embodiments of the invention described below, the alkylating agent is selected from the group consisting of an alkyl halide, an alkylsulfonate and an alkyleneimine.

According to another aspect of the present invention, there is provided an alternative process for preparing the compound having the general Formula I hereinabove, the process is effected by reacting a compound having the general Formula V:

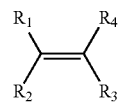

Formula V wherein:
$R_1$-$R_4$ are each independently an alkyl having from 1 to 20 carbon atoms;
with a compound having the general Formula VI:

Formula VI wherein:
X is halide or an alkyl having from 1 to 20 carbon atoms; and
X' is halide,
to thereby obtain a compound having the general Formula VII:

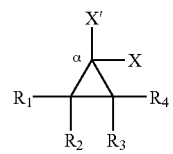

Formula VII and converting the compound having the general Formula VII to thereby obtain the compound having the general Formula III as presented herein; and
reacting the compound having the general Formula III with a compound having the general Formula IV as presented herein;
with the proviso that when X is halide, Y is O and A is N or O, at least one of $D_1$ and $D_2$ is selected from the group consisting of alkenyl, alkynyl, cycloalkyl, aryl, heteroaryl, hydroxy, alkoxy, hydroxyalkyl, thiohydroxy, thioalkoxy, thiohydroxyalkyl, aryloxy, thioaryloxy, haloalkyl, amine, carbonyl, amide, thioamide, carbamate, urea, alkyl-sulfonamide, aryl-sulfonamide, alkyl-aryl-sulfonamide, thiadiazole-sulfonamide, alkyl-thiadiazole-sulfonamide.

According to still further features in the described embodiments, the reaction between the compound having the general Formula V and the compound having the general Formula VI in the alternative process of preparing the compounds presented herein, is effected in the presence of an alkoxide-alcohol mixture. In some embodiments this mixture is tert-butoxide and tert-butanol mixture.

According to still further features in the described embodiments, the conversion of the compound having the general Formula VII in the alternative process of preparing the compounds presented herein, is effected in the presence of butyllithium and carbondioxide.

According to still further features in the described embodiments the process of preparing the compounds presented herein further includes, prior to the reacting the compound having the general Formula III with the compound having the general Formula IV, converting the compound having the general Formula III into a reactive carboxylic derivative thereof.

According to still further features in the described embodiments the reactive carboxylic derivative is an acyl-halide.

According to still further features in the described embodiments the process of preparing the compounds presented herein further includes, prior to the reacting the compound having general Formula II with the halogenating agent or alkylating agent, converting the compound having the general Formula II into an ester thereof, and subsequent to the reacting, hydrolyzing the ester to thereby obtain the compound having the general Formula III.

According to still further features in the described embodiments one or both of $D_1$ and $D_2$ includes a carbonyl, the carbonyl further includes an amine. According to some embodiments of the present invention one or both of $D_1$ and $D_2$ is moiety having the general Formula IX:

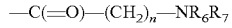 —C(=O)—(CH$_2$)$_n$—NR$_6$R$_7$  Formula IX whereas:

n is an integer from 0 to 20, and according to some embodiments n is 0; and $R_6$ and $R_7$ are each independently selected from the group consisting of hydrogen, alkyl, alkenyl, alkynyl, cycloalkyl, aryl, heteroaryl, halogen, hydroxy, alkoxy, hydroxyalkyl, thiohydroxy, thioalkoxy, thiohydroxyalkyl, aryloxy, thioaryloxy, haloalkyl, amine, carbonyl, amide, thioamide, carbamate, alkyl-sulfonamide, aryl-sulfonamide, alkyl-aryl-sulfonamide, thiadiazole-sulfonamide and alkyl-thiadiazole-sulfonamide, and according to some embodiments $R_6$ and $R_7$ are each independently hydrogen or alkyl. According to other embodiments one or more of $D_1$, $R_6$, and $R_7$ is methyl.

According to still further features in the described embodiments, one or both of $D_1$ and $D_2$ is alkoxy.

According to still further features in the described embodiments, one or both of $D_1$ and $D_2$ is thiadiazole-sulfonamide.

According to still further features in the described embodiments, $D_2$ is 5-yl-1,3,4-thiadiazole-2-sulfonamide.

According to still further features in the described embodiments either or both of $D_1$ or $D_2$ include a heteroaryl, according to some embodiments a heteroaryl substituted by a sulfonamide, and according to other embodiments $D_1$ or $D_2$ is a moiety having the general Formula X:

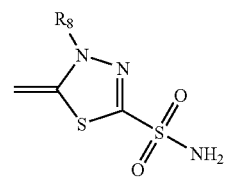

Formula X whereas $R_8$ is alkyl, and according to some embodiments $R_8$ is methyl.

According to still further features in the described embodiments, one or both of $D_1$ and $D_2$ is aryl-sulfonamide.

According to some embodiments of the present invention, Y is O and A is N, and according to other embodiments $D_1$ is hydrogen.

According to some embodiments of the present invention, each of $R_1$-$R_4$ is methyl.

According to some embodiments of the present invention, X is halide and according to other embodiments the halide is fluoride.

According to yet another aspect of the present invention there is provided a pharmaceutical composition comprising, as an active ingredient, a compound having the general Formula VIII:

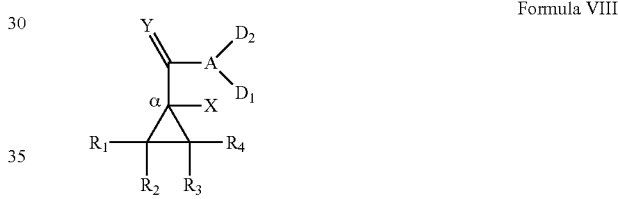

Formula VIII an enantiomer, a prodrug, a hydrate, a solvate or a pharmaceutically acceptable salt thereof and a pharmaceutically acceptable carrier;

wherein:

X is halide or an alkyl having from 1 to 20 carbon atoms;

$R_1$-$R_4$ are each independently an alkyl having from 1 to 20 carbon atoms;

Y is selected from the group consisting of $NR_5$, O and S;

A is selected from the group consisting of O, N and S;

$R_5$ is selected from the group consisting of hydrogen, alkyl and cycloalkyl; and $D_1$ and $D_2$ are each independently selected from the group consisting of hydrogen, alkyl, alkenyl, alkynyl, cycloalkyl, aryl, heteroaryl, halide, hydroxy, alkoxy, hydroxyalkyl, thiohydroxy, thioalkoxy, thiohydroxyalkyl, aryloxy, thioaryloxy, haloalkyl, amine, carbonyl, amide, thioamide, carbamate, alkyl-sulfonamide, aryl-sulfonamide, alkyl-aryl-sulfonamide, thiadiazole-sulfonamide, alkyl-thiadiazole-sulfonamide or absent.

According to further features in the embodiments of the invention described below, the pharmaceutical composition presented herein is being packaged in a packaging material and identified in print, in or on the packaging material, for use in the treatment of a neurological disease or disorder.

According to yet another aspect of the present invention there is provided a method of treating a neurological disease or disorder, the method is effected by administering to a subject in need thereof a therapeutically effective amount of a compound having the general Formula VIII.

According to yet another aspect of the present invention there is provided a use of a compound having general Formula VIII in the preparation of a medicament. According to some embodiments the medicament is for the treatment of a neurological disease or disorder.

According to further features in the embodiments of the invention described below, the neurological disease or disorder is selected from the group consisting of epilepsy, convulsions, and seizure disorders, status epilepticus, chemically-induced seizure or convulsions disorder, spasticity, skeletal muscle spasms, restless leg syndrome, anxiety, stress, multiple sclerosis, stroke, head trauma, spinal cord injury, amytrophic lateral sclerosis (ALS), Parkinson's Disease, Huntington's Disease, Alzheimer's Disease, amyotrophic lateral sclerosis, neuropathic pain, deafferentation pain, myoclonus, schizophrenia migraine, headaches and bipolar disorder. According to some embodiments, the neurological disease or disorder is epilepsy.

According to still further features in the described embodiments, the therapeutically effective amount ranges from about 0.1 mg/kg body to about 100 mg/kg body.

The present invention successfully addresses the shortcomings of the presently known configurations by providing α-halo- and α-alkyl-substituted cyclopropylcarboxy compounds which possess unique and novel features that render these compounds far superior to other cyclopropylcarboxy compounds known in the art, as therapeutic agents for treating epilepsy and other neurological disorders.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ ranges from" a first indicate number "to" a second indicate number are used herein interchangeably and are meant to include the first and second indicated numbers and all the fractional and integral numerals therebetween.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 presents the structures of Valproic acid and some of its derivatives which were tested as putative anticonvulsants in background art.

DESCRIPTION OF THE PREFERRED EMBODIMENTS

The present invention is of novel α-halo- and α-alkyl-substituted cyclopropanecarboxy compounds, and to processes of preparing same. The present invention is further of pharmaceutical compositions containing α-halo- and α-alkyl-substituted cyclopropanecarboxy compounds and uses thereof in the treatment of neurological diseases and disorders such as epilepsy.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, valproic acid and some derivatives and analogs thereof are well known for their beneficial therapeutic effect in the treatment of epilepsy and other central nervous system (CNS) diseases and disorders. For many decades researchers have manipulated the basic structure of valproic acid in an attempt to strike a new path to a more potent antiepileptic drug (AED).

These studies created a vast repository of compounds and processes for their preparation, amongst which is the family of tetramethylcyclopropane carboxylic acid (TMCA), which is regarded as an analogue of valproic acid.

In a search for a potent yet safer AEDs, having none or milder adverse side effects, the present inventors have designed a novel, unexplored path by preparing a series of derivatives of cyclopropylcarboxy compounds, which include a substituent at the α-position of the cyclopropane ring.

As demonstrated in the Examples section that follows, while reducing the present invention to practice, several α-halo- and α-alkyl-cyclopropylcarboxy compounds were prepared and successfully tested for their anticonvulsant activity in animal models.

Thus, according to one aspect of the present invention, there is provided a compound having the general Formula I:

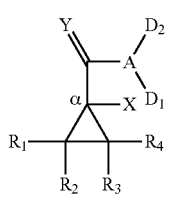

Formula I wherein:

X is a halide or an alkyl having from 1 to 20 carbon atoms;

$R_1$-$R_4$ are each independently an alkyl having from 1 to 10 carbon atoms;

Y is selected from the group consisting of $NR_5$, O and S;

A is selected from the group consisting of O, N and S; and $R_5$ is selected from the group consisting of hydrogen, alkyl and cycloalkyl; and $D_1$ and $D_2$ are each independently selected from the group consisting of hydrogen, an alkyl, an alkenyl, an alkynyl, a cycloalkyl, an aryl, a heteroaryl, a halogen, a hydroxy, an alkoxy, a hydroxyalkyl, a thiohydroxy, a thioalkoxy, a thiohydroxyalkyl, an aryloxy, a thioaryloxy, a haloalkyl, an amine, a carbonyl, an amide, a thioamide, a carbamate, an alkyl-sulfonamide, an aryl-sulfonamide, an alkyl-aryl-sulfonamide, a thiadiazole-sulfonamide and an alkyl-thiadiazole-sulfonamide, as these terms are defined herein, or absent;

with the proviso that when X is halide, Y is O and A is N or O, at least one of $D_1$ and $D_2$ is selected from the group consisting of alkenyl, alkynyl, cycloalkyl, aryl, heteroaryl, hydroxy, alkoxy, hydroxyalkyl, thiohydroxy, thioalkoxy, thiohydroxyalkyl, aryloxy, thioaryloxy, haloalkyl, amine, carbonyl, amide, thioamide, carbamate, urea, alkyl-sulfonamide, aryl-sulfonamide, alkyl-aryl-sulfonamide, thiadiazole-sulfonamide, alkyl-thiadiazole-sulfonamide.

It is noted herein that each of $D_1$ and $D_2$, independently, can be attached to A via a single bond or a double bond, depending on the nature of $D_1$ and $D_2$ and the valency of A. Thus, for example, in cases where A is N, and $D_1$ is absent, $D_2$ can be attached to the nitrogen via a double bond.

It is further noted that the feasibility of each of the substituents (X, Y, A, $D_1$, $D_2$ and $R_1$-$R_5$) to be located at the indicated positions depends on the valency and chemical compatibility of the substituent, the substituted position and other substituents. Hence, the present invention is aimed at encompassing all the feasible substituents for any position.

The compounds described herein are therefore based on the active TMCA analogue of valproic acid (VPA), which is substituted at the α-position of the cyclopropane ring by a halide or alkyl.

As used herein, the terms "halo" and "halide", which are referred to herein interchangeably, describe an atom of a fluorine, chlorine, bromine or iodine, also referred to herein as fluoride, chloride, bromide and iodide.

As used herein, the term "alkyl" describes an aliphatic hydrocarbon including straight chain and branched chain groups. According to some embodiments, the alkyl group has 1 to 10 carbon atoms, and according to other embodiments 1-4 carbon atoms. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. The alkyl can be substituted or unsubstituted. When substituted, the substituent can be, for example, an alkyl, an alkenyl, an alkynyl, a cycloalkyl, an aryl, a heteroaryl, a halogen, a hydroxy, an alkoxy, a hydroxyalkyl, a thiohydroxy, a thioalkoxy, a thiohydroxyalkyl, an aryloxy, a thioaryloxy, a haloalkyl, an amine, a carbonyl, an amide, a thioamide, a carbamate, an alkyl-sulfonamide, an aryl-sulfonamide, an alkyl-aryl-sulfonamide, a thiadiazole-sulfonamide and an alkyl-thiadiazole-sulfonamide, as these terms are defined hereinbelow.

The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

According to some embodiments, when X is alkyl, the alkyl is a lower alkyl, having 1-10, according to other embodiments 1-4 carbon atoms. According to some embodiments, when X is alkyl, the alkyl is a saturated alkyl and according to other embodiments, a saturated, unsubstituted alkyl (e.g., methyl).

The cyclopropane ring is further substituted by alkyls, represented by $R_1$-$R_4$ in Formula I hereinabove. $R_1$, $R_2$, $R_3$ and $R_4$ can be the same or different and each is independently an alkyl having 1-10 carbon atoms. According to some embodiments, each of $R_1$-$R_4$ is a lower alkyl, having 1-10 carbon atoms and, according to other embodiments, 1-4 carbon atoms. According to yet other embodiments, each of $R_1$-$R_4$ is methyl. As discussed hereinabove, 2,2,3,3-tetramethylcyclopropane is an analogue of valproic acid and hence structurally analogous thereto and thus exhibits similar therapeutic activity.

According to some embodiments of the present invention X is halide, and according to other embodiments, X is fluoride.

Further in analogy to VPA and TMCA, Y can be O (oxygen atom), S (sulfur atom) or $NR_5$, and A can be O, S or N (nitrogen atom), such that together they constitute a part of a carboxy moiety.

The phrase "carboxy moiety" is used herein to collectively describe chemical moieties which are derivatives or analogues of a carboxylate, as defined herein, and encompasses all the feasible chemical combinations of Y and A as defined herein, such as, for example, an amide, a thiocarboxylate, a dithiocarboxylate, a thioamide, an imide or an N-substituted imide, a thioimide and an amidine, as these terms are defined herein.

The compounds described herein are therefore referred to as "cyclopropylcarboxy compounds" or "cyclopropanecarboxy compounds", interchangeably. These compounds, however, can also be referred to as "cyclopropylcarbonyl compounds" and "cyclopropanecarbonyl compounds", thus representing in their name the —C=Y moiety in general Formula I hereinabove, which can be further substituted by the -A(D₁)(D₂) moiety in Formula I above.

It will be appreciated by one of skills in the art that the feasibility of each of the substituents (R₁₋₄, R₅, X, Y, A, D₁ and D₂) to be located at the indicated positions depends on the valency and chemical compatibility of the substituent, the substituted position and other substituents. Hence, the present invention is aimed at encompassing all the feasible substituents for any position. For example, in cases where A is O or S, D₁ is absent and D₂ is as defined herein. In cases where A is N, both D₁ and D₂ are present unless one of D₁ and D₂ is attached to A via a double bond, in which case the other one of D₁ and D₂ is absent.

When Y and A are both O, the compound is a carboxylate, as defined herein.

The term "carboxylate", as used herein, refers to a —C(=O)—O—R', where R' is selected from the group consisting of hydrogen, alkyl, cycloalkyl, heteroalicyclic, aryl or heteroaryl, as these terms are defined herein.

When Y is O and A is N, the compound is an amide, as defined herein.

The term "amide" describes a —C(=O)—NR'R", where R' is as defined herein and R" is as defined for R'.

When Y is N and A is O, the compound is an imide, as defined herein.

As used herein the term "imide" refers to a —C(=NR')—O—R" group, where R' and R" are as defined herein.

When Y and A are both N, the compound is an amidine, as defined herein.

As used herein the term "amidine" refers to a —C(=NR')—NR"R'" group, where R' and R" are as defined herein, and R'" is as defined for R'.

When Y is O or S and A is S or O respectively, the compound is a thiocarboxylate, as defined herein.

The term "thiocarboxylate", as used herein, refers to a —C(=O)—S—R', where R' is as defined herein. When R' is an alkyl, the thiocarboxylate is referred to as a thiocarboxylate-S-alkyl ester, and when the group is —C(=S)—O—R', the thiocarboxylate is referred to as a thiocarboxylate-O-alkyl ester.

When Y and A are both S, the compound is a dithiocarboxylate, as defined herein.

The term "dithiocarboxylate", as used herein, refers to a —C(=S)—S—R', where R' is as defined herein.

When Y is S and A is N, the compound is a thioamide, and when Y is N and A is S, the compound is a thioimide, as these terms are defined herein.

The term "thioamide" describes a —C(=S)—NR'R", where R' is as defined herein and R" is as defined for R'.

The term "thioimide" describes a —C(=NR')—SR", where R' and R" are as defined herein.

In some embodiments of the present invention, Y is O and the carboxy moiety defined by —C(=Y)-A- in the formula above is amide, thicaboxylate or ester. According to other embodiments, Y is O and A is N, and the carboxy moiety is amide.

According to the present embodiments, compounds in which X is halide, Y is O and A is O or N, namely compounds which are an ester or an amide derivative of TMCA, and further wherein D₁ and D₂ are hydrogen, methyl or other low alkyls, are excluded from the scope of this aspect of the present invention. As mentioned hereinabove, such compounds have been previously prepared. Nonetheless, none of these compounds was described or tested in the context of therapeutic agents. These compounds are therefore not excluded from other aspects of the present invention.

According to some embodiments, D₁ and D₂ are each independently selected from the group consisting of hydrogen, an alkyl, an alkenyl, an alkynyl, a cycloalkyl, an aryl, a heteroaryl, a halogen, a hydroxy, a hydroxyalkyl, a thiohydroxy, a thioalkoxy, a thiohydroxyalkyl, an aryloxy, a thioaryloxy, a haloalkyl, an amine, a carbonyl, an amide, a thioamide, a carbamate, an alkyl-sulfonamide, an aryl-sulfonamide, an alkyl-aryl-sulfonamide, a thiadiazole-sulfonamide and an alkyl-thiadiazole-sulfonamide, as these terms are defined herein, or absent.

The term "cycloalkyl", as used herein, describes an all-carbon monocyclic or fused ring (i.e., rings which share an adjacent pair of carbon atoms) group where one or more of the rings does not have a completely conjugated pi-electron system. The cycloalkyl may be substituted or unsubstituted by one or more substituents. When substituted, the substituent can be, for example, an alkyl, an alkenyl, an alkynyl, a cycloalkyl, an aryl, a heteroaryl, a halogen, a hydroxy, a hydroxyalkyl, a thiohydroxy, a thioalkoxy, a thiohydroxyalkyl, an aryloxy, a thioaryloxy, a haloalkyl, an amine, an amide, a thioamide, a carbamate and urea, as these terms are defined herein.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted by one or more substituents, as described hereinabove. Representative examples of heteroalicyclics include, without limitation, piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted by one or more substituents, as described hereinabove.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

As used herein, the term "amine" describes a —NR'R" group where each of R' and R" is independently hydrogen, alkyl, cycloalkyl, heteroalicyclic, aryl or heteroaryl, as these terms are defined herein.

The term "hydroxyl", as used herein, refers to an —OH group.

The term "hydroxyalkyl" describes a —R'—OH group, where R' is as defined herein.

The term "thiohydroxy", as used herein, refers to an —SH group.

The term "thioalkoxy" describes a —SR' group, where R' is as defined herein.

The term "thiohydroxyalkyl" describes a —R'—SH group, where R' is as defined herein.

The term "haloalkyl" describes an alkyl group as defined above, further substituted by one or more halide(s).

The term "carbamate" describes an —OC(=O)—NR'R", with R' and R" as defined herein.

The term "urea" as used herein, refers to a —NR'C(=O)—NR"R'", where R' and R" are as defined herein, and R'" is as defined herein for R' and R".

As discussed hereinabove, studies have shown that when the carboxy moiety of VPA and TMCA, as well as analogs thereof, was further substituted by particular substituents, improved therapeutic effect was achieved. These substituents include alkoxy, carbonyls, and particularly various derivatives of sulfonamides.

Hence, in some embodiments, at least one of $D_1$ and $D_2$ is selected from the group consisting of an alkoxy, a carbonyl, an alkyl-sulfonamide, an aryl-sulfonamide, an alkyl-aryl-sulfonamide, a thiadiazole-sulfonamide and an alkyl-thiadiazole-sulfonamide, as these terms are defined herein.

According to some embodiments, at least one of $D_1$ and $D_2$ is an alkoxy.

The term "alkoxy" describes a —OR' group, where R' is as defined herein.

The term "carbonyl", or "ketone", as used herein, refers to —(C=O)—R', where R' is as defined herein.

According to some embodiments, at least one of $D_1$ and $D_2$ is an amino-substituted carbonyl.

As used herein, the phrase "amino-substituted carbonyl" describes a carbonyl group, as defined herein, in which R' is an alkyl, cycloalkyl or heteroalicyclic, aryl or heteroaryl, as these terms are defined herein, which is further substituted by an amine group, as defined herein.

In one non-limiting example, at least one of $D_1$ and $D_2$ is an amino-substituted carbonyl which has the general Formula IX:

—C(=O)—(CH$_2$)$_n$—NR$_6$R$_7$    Formula IX whereas n is an integer from 0 to 20; and $R_6$ and $R_7$ are each independently selected from the group consisting of hydrogen, an alkyl, an alkenyl, an alkynyl, a cycloalkyl, an aryl, a heteroaryl, a halogen, a hydroxy, an alkoxy, a hydroxyalkyl, a thiohydroxy, a thioalkoxy, a thiohydroxyalkyl, an aryloxy, a thioaryloxy, a haloalkyl, an amine, a carbonyl, an amide, a thioamide, a carbamate, an alkyl-sulfonamide, an aryl-sulfonamide, an alkyl-aryl-sulfonamide, a thiadiazole-sulfonamide and an alkyl-thiadiazole-sulfonamide, as these terms are defined herein. According to some embodiments, $R_6$ and $R_7$ are each independently hydrogen and alkyl, and according to other embodiments, $R_6$ and $R_7$ are each hydrogen and methyl.

Further according to some embodiments of the present invention, at least one of $D_1$ or $D_2$ is a sulfonamide, and according to other embodiments one or more of an alkyl-sulfonamide, aryl-sulfonamide and an alkyl-aryl-sulfonamide. According to yet other embodiments, at least one of $D_1$ and $D_2$ is aryl-sulfonamide.

The term "sulfonamide" describes an —S(=O)$_2$—NR'R", with R' and R" as defined herein.

The term "alkyl-sulfonamide" as used herein, refers to a —R'—S(=O)$_2$—NR'R", where R' and R" are as defined herein, and R'" is as defined herein for R' and R".

The term "aryl-sulfonamide" as used herein, refers to a -aryl-S(=O)$_2$—NR'R", with R' and R" as defined herein.

The term "alkyl-aryl-sulfonamide" as used herein, refers to a —R'-aryl-S(=O)$_2$—NR'R", where R' and R" are as defined herein, and R'" is as defined herein for R' and R".

According to some embodiments of the present invention, at least one of $D_1$ or $D_2$ is a heteroaryl, and according to other embodiments a thiadiazole.

In the abovementioned studies on VPA and TMCA analogs, the combination of a thiadiazole and a sulfonamide as one of the substituents for the carboxy moiety thereof afforded highly active compounds. Hence, according to some embodiments of the present invention, at least one of $D_1$ or $D_2$ is selected from the group consisting of a thiadiazole-sulfonamide and an alkyl-thiadiazole-sulfonamide.

The term "thiadiazole-sulfonamide", as used herein, refers to a thiadiazole substituted with a sulfonamide, as these terms are defined herein, whereby according to some embodiments, the sulfonamide substituent is attached at the 5-position of the thiadiazole.

The term "alkyl-thiadiazole-sulfonamide", as used herein, refers to an —R'-thiadiazole-sulfonamide, with R' as defined herein. According to some embodiments R' is attached at the 3-position of the thiadiazole and the sulfonamide substituent is attached at the 5-position of the thiadiazole.

In one non-limiting example, one of $D_1$ and $D_2$ is absent and the other is a thiadiazole-sulfonamide which is attached to A via a double bond, as represented by the general Formula X:

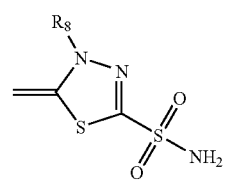

Formula X whereas $R_8$ is alkyl. According to some embodiments, $R_8$ is methyl.

According to some embodiments of the present invention $D_1$ is hydrogen, whereby $D_2$ is as described hereinabove.

Table 1 hereinbelow presents exemplary α-halo- and α-alkyl-cyclopropylcarboxy compounds according to some embodiments of the present invention.

The present embodiments further encompass any enantiomers, prodrugs, solvates, hydrates and/or pharmaceutically acceptable salts of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. An example, without limitation, of a pharmaceutically acceptable salt would be a carboxylate anion and a cation such as, but not limited to, ammonium, sodium, potassium and the like.

Further according to the present invention, there is provided a process of preparing the compounds presented hereinabove, as described and demonstrated in the Examples section that follows under General Procedure 1. The process is generally effected by introducing the X substituent, as defined hereinabove, at the α-position of a cyclopropane carboxylic acid compound, and converting the resulting α-substituted cyclopropane to the desired carboxy derivative thereof.

Thus, as a starting material, a suitable cyclopropylcarboxy compound is provided, which is represented by the general Formula II below:

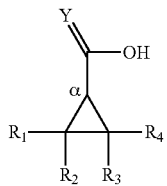

Formula II

Depending on the desired X, namely a halide or an alkyl, the compound having the general Formula II is reacted with a halogenating agent or an alkylating agent, respectively, to thereby obtain a compound having the general Formula III:

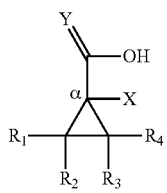

Formula III

In cases where X is halide, the compound having general Formula II is reacted with a halogenating agent.

The phrase "halogenating agent", as used herein, refers to a chemical reagent which use thereof can place a halide, as this is define herein, at a designated position on a given reactant compound.

Examples of commonly used halogenating agents for this purpose include, without limitation, fluorination agents such as N-fluorobenzenesulfonimide and 1-fluoropyridinium triflate, chlorination agents such as $Cl_2$ and N-chlorosuccinimide, bromination agents such as $Br_2$, N-bromosuccinimide and 1,3-Dibromo-5,5-dimethylhydantoin, and iodination agents such as $I_2$ and N-Iodosuccinimide. According to some embodiments, the halogenating agent is benzenesulfonyl halide (N-halobenzenesulfonimide).

In cases where X is alkyl, the compound having general Formula II is reacted with an alkylating agent.

The phrase "alkylating agent", as used herein, refers to a chemical reagent which use thereof can place an alkyl, as this is define herein, at a designated position on a given reactant compound.

Examples of known alkylating agents include, without limitation, an alkylsulfonate, an alkyleneimine, phosgene, alkyl tosylates such as methyl tosylate, alkyl triflates such as methyl triflate, alkyl halides such as methyl bromide and methyl iodide, trimethyloxonium tetrafluoroborate, dialkyl sulfate, alumoxanes, trialkylaluminum and tris(trialkylyl)aluminum.

Non-limiting examples of alumoxanes include methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO).

Non-limiting examples of trialkylaluminum and tris(trialkylyl)aluminum alkylating agents include trimethylaluminum (TMA), tris(2,4,4-trimethyl-pentyl)aluminum (TIOA), tris(2-methyl-propyl)aluminum (TIBA), tris(2,3,3-trimethylbutyl)aluminum, tris(2,3-dimethyl-hexyl)aluminum, tris(2,3-dimethyl-butyl)aluminum, tris(2,3-dimethyl-pentyl)aluminum, tris(2,3-dimethyl-heptyl)aluminum, tris(2-methyl-3-ethyl-pentyl)aluminum and tris(2-ethyl-3,3-dimethyl-butyl).

According to some embodiments of the present invention, the carboxy moiety present in the compound having the general Formula II, represented by —C(═Y)—OH, is protected prior to the reaction with the halogenating agent or alkylating agent. According to some embodiments, the carboxy moiety is converted into an ester thereof, as this is defined herein. The ester can be hydrolyzed back into a carboxylic acid subsequent to the reaction with the halogenating agent or alkylating agent.

Arriving at a compound having the general Formula III can be achieved by an alternative route. Hence, according to another aspect of the present invention, there is provided an alternative process for preparing the compound having the general Formula I hereinabove.

This process is effected by reacting a compound having the general Formula V:

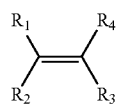

Formula V wherein:
$R_1$-$R_4$ are as defined herein;
with a compound having the general Formula VI:

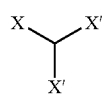

Formula VI wherein:

X is halide or an alkyl having from 1 to 20 carbon atoms; and

X' is halide, to thereby obtain cyclopropane-derivative compound the general Formula VII:

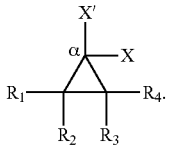

Formula VII

Thereafter, this cyclopropane-derivative compound is converted into the acid compound having the general Formula III as presented herein.

According to some embodiments of the present invention, the reaction for forming this cyclopropane-derivative compound is effected in the presence of an alkoxide-alcohol mixture.

The phrase "alkoxide-alcohol mixture", as used herein, refer to a mixture of an organic alkoxide in the form of a $R^*$—$O^-$ group and the corresponding alcohol in the form of $R^*$—OH, wherein $R^*$ is an alkyl, as defined herein. The alkoxide-alcohol mixture is widely used as a basic reagent mixture in organic syntheses to extract a hydrohalogenic acid from a reaction mixture such as a cyclization reaction between an alkene and a haloform (trihalomethanes), which typically lead to the formation of a cyclopropane-derivative compound. According to some embodiments of the present invention, this alkoxide-alcohol mixture is a tert-butoxide and tert-butanol mixture.

According to some embodiments of the present invention, the conversion of the compound having the general Formula VII is effected in the presence of butyllithium and carbondioxide.

A detailed and exemplified description of this alternative process for preparing the compounds presented herein is provided in the Examples section that follows, under General Procedure 2.

Once the compound having the general Formula III is formed, the conversion to a compound having the general Formula I is effected in a variety of processes, many of which are described in the art which deals with converting tetramethylcyclopropylcarboxylic acid into a variety of tetramethylcyclopropylcarboxy derivatives [10-17, 20-26].

Briefly, converting a cyclopropane carboxylic acid compound to various carboxy derivatives thereof can be effected via a variety of simple or complex chemicals reaction, which are generally aimed at converting the carboxylate into an amide, an ester, an imide etc., and the respective substituted derivatives, as detailed hereinabove.

According to an exemplary embodiment of this aspect of the present invention, the conversion of the compound having the general Formula III (carboxylic acid) into the compound having the general Formula I, in which the carboxy moiety is, for example, an amide, is effected by converting the compound having the general Formula III into a reactive form of a carboxylic acid. Representative examples of such reactive forms of a carboxy moiety include, without limitation, carboxyl-halides or acyl-halides, carboxyl-anhydride or acyl-anhydride, carboxylic esters and the likes. According to some embodiments, the reactive form of a carboxylic acid is an acyl-halide.

As used herein, the term "carboxyl-halide" or "acyl-halide", refers to a —(C=Y)—X', wherein Y is as defined herein and X' is halide.

As used herein, the term "carboxyl-anhydride" or "acyl-anhydride", refers to a —(C=Y)—O—(C=O)—R', wherein Y and R' are as defined herein.

The term "carboxylic ester", as used herein, refers to a —(C=Y)—O—R', wherein Y and R' are as defined herein.

In some embodiments, the compound having the general Formula III is reacted with a compound having the general Formula IV:

Formula IV wherein A, D1 and D2 are as defined hereinabove.

The compound having the general Formula IV is selected such that upon the reaction thereof with a compound having the general Formula III, or an activated form thereof, a compound having the desired substituents with respect to $D_1$ and $D_2$ is afforded.

For another example, if the desired compound is Compound 2 (see, Table 1 hereinbelow), the corresponding compound having the general Formula IV is methyl amine.

For another example, if the desired compound is Compound 3 (see, Table 1 hereinbelow), the corresponding compound having the general Formula IV is urea, which can be regarded as formamide-amine.

For yet another example, if the desired compound is Compound 6 (see, Table 1 hereinbelow), the corresponding compound having the general Formula IV is 5-amino-[1,3,4]thiadiazole-2-sulfonic acid amide.

As discussed hereinabove, the present inventors have envisioned that α-substituted cyclopropylcarboxy compounds of the present invention would exhibit therapeutic activity at least similar and preferably improved, compared with valproic acid and TMCA, and hence these compounds were developed as, for example, potential antiepileptic drugs. While reducing the present invention to practice, as is demonstrated in the Examples section that follows, it was indeed shown that exemplary compounds as presented herein were tested for anticonvulsant as were indeed found to be highly active, mostly in a dose-dependent manner.

Based on the therapeutic activity exhibited by these compounds, according to another aspect of the present invention there is provided a use of α-halo or α-alkyl substituted cyclopropylcarboxy compounds, as represented in the general Formula VIII:

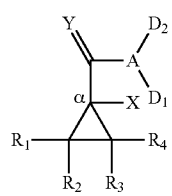

Formula VIII

Wherein:

X is a halide or an alkyl having from 1 to 20 carbon atoms, as defined herein;

$R_1$-$R_4$ are each independently an alkyl having from 1 to 10 carbon atoms;

Y is selected from the group consisting of $NR_5$, O and S;

A is selected from the group consisting of O, N and S; and $R_5$ is selected from the group consisting of hydrogen, alkyl and cycloalkyl; and $D_1$ and $D_2$ are each independently selected from the group consisting of hydrogen, an alkyl, an alkenyl, an alkynyl, a cycloalkyl, an aryl, a heteroaryl, a halogen, a hydroxy, an alkoxy, a hydroxyalkyl, a thiohydroxy, a thioalkoxy, a thiohydroxyalkyl, an aryloxy, a thioaryloxy, a haloalkyl, an amine, a carbonyl, an amide, a thioamide, a carbamate, an alkyl-sulfonamide, an aryl-sulfonamide, an alkyl-aryl-sulfonamide, a thiadiazole-sulfonamide and an alkyl-thiadiazole-sulfonamide, as these terms are defined herein, or absent, as well enantiomers, hydrates, solvates or pharmaceutically acceptable salts thereof, as defined hereinabove, in the preparation of a medicament.

According to some embodiments, the medicament is for treating a neurological disease or disorder.

Accordingly, according to another aspect of the present invention, there is provided a method of treating a neurological disease or disorder. The method is effected by administering to a subject in need thereof a therapeutically effective amount of α-halo or α-alkyl substituted cyclopropylcarboxy compounds as represented in general Formula VIII above.

As used herein, the terms "treating" and "treatment" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "neurological disease or disorder" refers to a genetic or acquired dysfunction in one of the component of the brain and spinal cord, namely the central nervous system (CNS), peripheral and cranial nerves (PNS), namely the peripheral nervous system or the autonomic nervous system and the musculoskeletal system. These diseases and disorders express themselves in a variety of behavioral symptoms, motorial symptoms, form disfigurements (deformity, abnormality), neuropathic pain and cognitive disturbances and other physiological symptoms. In the context of the present invention, neurological diseases and disorders include psychiatric diseases and disorders and neurodegenerative diseases and disorders.

According to an exemplary embodiment of the present invention, the neurological disorder comprises seizures, relating to any abnormal electrical discharge in the brain resulting in abnormal synchronization of electrical neuronal activity. Seizures may be due to epilepsy and non epilepsy associated.

For example non epileptic seizures can be caused by chemical agents. As used herein, the phrase "chemically-induced convulsions and/or seizure disorder" refers to a seizure caused by temporary or chronic exposure to an exogenic substance or chemical such as, for example, a toxin (such as, for example, tetanus toxin (tetanospasmin), botulin, tetrodotoxin, batrachotoxin, maurotoxin, agitoxin, charybdotoxin, margatoxin, slotoxin, scyllatoxin, hefutoxin, calciseptine, taicatoxin and calcicludine), an alkaloid (such as ephedrine alkaloids, phenethylamines, amphetamines, tryptamines, mescaline, psilocybin and pilocarpine), a nerve agent, an and an organophosphate (such as, for example, tabun (GA), sarin (GB), soman (GD), cyclosarin (GF), GV, VE, VG, VM, VX, Novichok agents, pulmonary agents, chloropicrin (PS), phosgene (CG) and diphosgene (DP)) and a drug (such as, for example, aminophylline or local anaesthetics as well as antidepressants).

Other seizures without epilepsy include but are not limited to those induced by fever leading to febrile convulsions, metabolic disturbances such as hypoglycemia hyponatremia or hypoxia, sustenance withdrawal (e.g., GHB and derivatives thereof, as well as benzodiazepines, ethanol and baclofen), eclampsia, binaural beat brainwave entertainment. Others are listed hereinbelow.

Thus, examples of neurological diseases and disorders include, without limitation, altered mental status, encephalopathy, stupor and coma, fever (febrile convulsions), cerebral palsy, cerebrovascular disease such as transient ischemic attack and stroke, demyelinating diseases such as multiple sclerosis, Guillain-Barré syndrome and chronic inflammatory demyelinating polyneuropathy (CIDP), epilepsy and seizure disorders, headache disorders such as migraine, cluster headache and tension headache, infections of the brain (encephalitis), brain meninges (meningitis), spinal cord (myelitis), movement disorders such as in Parkinson's disease, Huntington's disease, hemiballismus, tic disorder, and Gilles de la Tourette syndrome, CNS neoplasms (brain tumors), spinal cord tumors, PNS tumors, sleep disorders, speech and language disorders, spinal cord disorders such as tumors, infections, trauma, malformations (e.g., myelocele, meningomyelocele tethered cord), traumatic injuries to the brain, spinal cord and PNS, disorders of peripheral nerves, muscle (myopathy) and neuromuscular junctions, deafferentation pain (also called phantom pain, anesthesia dolorosa or denervation pain), various infections of the PNS such as botulism.

Examples of psychiatric diseases and disorders include, without limitation, psychotic disorders or diseases such as schizophrenia, anxiety disorders, dissociative disorders, personality disorders, mood disorders such as depression, affective disorders including unipolar and bipolar disorders, boarder line disorders and mental diseases or disorders.

Examples of neurodegenerative diseases and disorders include, without limitation, Alexander disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Huntington disease, HIV-associated dementia, Kennedy's disease, Krabbe disease, Lewy body dementia, Machado-Joseph disease (Spinocerebellar ataxia type 3), Multiple sclerosis, Multiple System Atrophy (MSA), Parkinson's disease, Pelizaeus-Merzbacher Disease, Pick's disease, Primary lateral sclerosis, Refsum's disease, Sandhoff disease, Schilder's disease, Schizophrenia, Spielmeyer-Vogt-Sjogren-Batten disease (also known as Batten disease), Spinocerebellar ataxia (multiple types with varying characteristics), Spinal muscular atrophy, and Steele-Richardson-Olszewski disease.

The neurological disease or disorder, according to some embodiments of the present invention, is selected from the group consisting of epilepsy, convulsions, and seizure disorders, status epilepticus, a chemically-induced convulsion and/or seizure disorder, a febrile convulsion condition, a metabolic disturbance, a sustenance withdrawal condition, spasticity, skeletal muscle spasms, restless leg syndrome, anxiety, stress, multiple sclerosis, stroke, head trauma, spinal cord injury, (ALS), Parkinson's Disease, Huntington's Disease, Alzheimer's Disease, amyotrophic lateral sclerosis, neuropathic pain, myoclonus, schizophrenia, migraine, headaches and bipolar disorders. According to some embodiments of the present invention, the compounds described herein are utilized for treating epilepsy.

According to further embodiments of the present invention, the compounds described herein are utilized for treating neuropathic pain, phantom pain, migraine, schizophrenia and a bipolar disorder.

As used herein, the phrase "therapeutically effective amount" describes an amount of the compound being administered which will relieve to some extent one or more of the symptoms of the condition being treated.

As demonstrated in the examples section that follows, an exemplary therapeutically effective amount of the compounds of the present invention ranges between about 0.1 mg/kg body and about 100 mg/kg body.

As used herein throughout the term "about" refers to ±10%.

In any of the methods and uses described herein, the α-halo or α-alkyl substituted cyclopropylcarboxy compounds of the present embodiments can be utilized either per se or, according to some embodiments, as a part of a pharmaceutical composition that further comprises a pharmaceutically acceptable carrier.

Thus, according to additional aspects of the present invention, there is provided pharmaceutical composition, which comprises one or more compounds having the general Formula VIII, as defined hereinabove, and a pharmaceutically acceptable carrier.

As used herein a "pharmaceutical composition" refers to a preparation of the compounds presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of a neurological disease or disorder, as is detailed hereinabove.

Thus, according to an embodiment of the present invention, the pharmaceutical composition of the present invention is being packaged in a packaging material and identified in print, in or on the packaging material, for use in the treatment of a neurological disease or disorder, as is defined hereinabove.

According to further embodiments of the any of the methods, uses and compositions presented herein, the compounds of the present invention can be combined with other active ingredients which are commonly used to treat neurological diseases and disorders.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions; illustrate the invention in a non limiting fashion.

Example 1

Chemical Synthesis

Materials and Methods:

2,2,3,3-tetramethylcyclopropanecarboxylic acid (TMCA) was obtained from Sigma-Aldrich.

N-fluorobenzenesulfonimide was purchased from Fluorochem, UK.

Other chemicals, solvents and reagents were purchased from Sigma-Aldrich.

Melting point was measured using Buchi 530 Capillary melting point apparatus.

Thin layer chromatography (TLC) analysis was performed using pre-coated silica gel on aluminum sheets Kieselgel 60 $F_{254}$, by Merck.

NMR measurements were performed using Varian mercury series NMR 300 spectrometer.

GC-MS measurements were performed using HP 5890 SEIES II GC equipped with a Hewlett-Packard ms engine (HP5989A) single quadropole, MS spectrometer, HP7673 auto-sampler, HP MS-DOS Chemstation and HP-5MS capillary column (0.25 μm×15 m×0.25 mm).

Preparation of α-halo-2,2,3,3-tetramethylcyclopropanecarboxylic acid (α-halo-TMCA)—General Procedure 1

The general synthetic pathway for preparing α-halo-TMCA is depicted in Scheme 1 below:

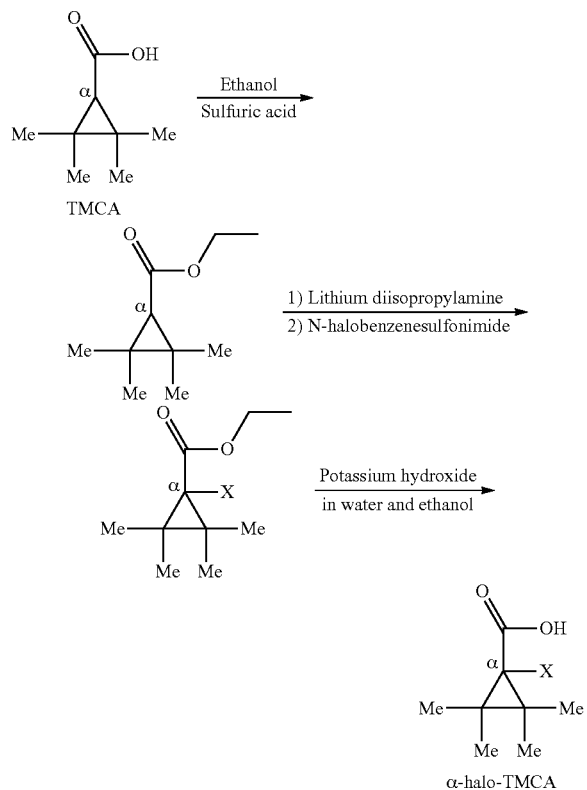

(X = F, Cl, Br or I)

As can be seen in Scheme 1, an ethyl ester of 2,2,3,3-tetramethylcyclopropanecarboxylic acid (TMCA) is prepared by refluxing the acid with ethyl alcohol in an excess ratio of 1:15 in the presence of a catalytic amount of sulfuric acid. The unreacted alcohol is thereafter removed under reduced pressure and the reaction mixture is dissolved in 100 ml of hexane, washed with sodium hydroxide and brine, dried over sodium sulfate and filtered. The organic solvent is evaporated and the ester, typically afforded as a colorless liquid, is further purified by vacuum distillation.

A solution of lithiumdiisopropylamine (LDA, 0.032 moles) is prepared by dissolving diisopropylamine in freshly distilled tertahydrofuran (THF distilled over calcium hydride) under nitrogen. The reaction mixture is cooled to −15° C. and butyl lithium (BuLi, 0.032 moles) is added slowly thereto while stirring and maintaining the temperature of the mixture at −15° C. The resulting mixture is then stirred and cooled for additional ten minutes, and thereafter allowed to warm to 0° C. while stirring for additional ten minutes. Thereafter the reaction mixture is cooled again to −15° C., TMCA ethyl ester (0.03 moles), dissolved in dry THF is added thereto and the mixture was stirred for 40 minutes.

Thereafter, the temperature is elevated to about −8° C., and 1.5 equivalents of the halobenzenesulfonimide reagent dissolved in dry THF are added to the reaction mixture.

The reaction mixture is stirred for additional 30 minutes while the formation of α-halo-TMCA ethyl ester is monitored by GC-MS. Once the reaction is completed the organic solvent is removed under reduced pressure and the typically oily residue is dispersed in ethyl acetate and filtered twice on a Buchner funnel. The solids in the funnel are washed twice with hexane, the hexane and ethyl acetate are combined and washed with water, HCl (1N) and brine, dried over sodium sulfate and filtered. The solvent is evaporated to yield α-halo-TMCA ethyl ester typically as a yellow oil.

The α-halo-TMCA ethyl ester is hydrolyzed to the corresponding acid using potassium hydroxide (0.045 moles) in a water:ethanol mixture (1:1, v/v), while monitoring the hydrolysis progress by GC-MS. Once the reaction is completed, the ethanol is evaporated, the remaining aqueous solution is washed with hexane, and the organic fraction is discarded. The aqueous solution is cooled and slowly acidified to pH 1 using HCl 1N, and thereafter extracted three times with ethyl acetate. The organic extracts are combined and washed three times with 5% sodium bicarbonate solution, and the combined sodium bicarbonate solutions are acidified to pH 1 and extracted with ethyl acetate. The organic fraction is dried over sodium sulfate and filtered, and the solvent is evaporated to yield α-halo-TMCA typically as a white powder.

The chemical structure of the obtained α-halo-TMCA is verified by spectroscopic methods (NMR, GC-MS), the purity of the product is assessed by TLC and by elemental analysis, and a typical yield of the entire process is about 50%.

Preparation of α-halo-2,2,3,3-tetramethylcyclopropanecarboxylic acid (α-halo-TMCA)—General Procedure 2

Another general synthetic pathway for preparing α-halo-TMCA is depicted in Scheme 12 below:

Scheme 2

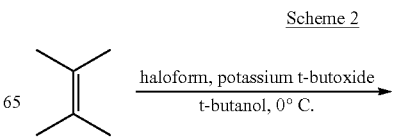

-continued

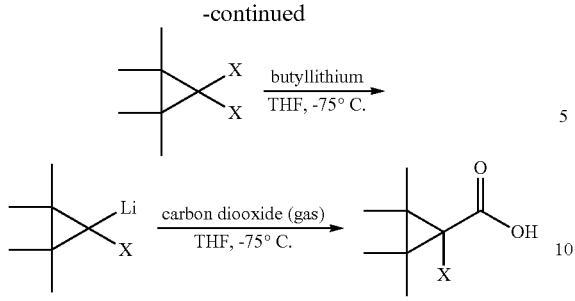

As can be seen in Scheme 2, 2,3-dimethyl 2-butene is reacted with a haloform compound such as chloroform or iodoform, in the presence of potassium tert-butoxide in tert-butanol, at 0° C. The reaction mixture is stirred overnight and is allowed to warm to room temperature. The solvent is removed under reduced pressure and the reaction mixture dissolved in petroleum ether is washed three times with water and brine, dried over magnesium sulfate and filtered. The solvent is removed under reduced pressure to give the 1,1-dihalo-2,2,3,3-tetramethylcyclopropane as a white solid.

The resulting 1,1-dihalo-2,2,3,3-tetramethylcyclopropane is thereafter dissolved in freshly distilled tertahydrofuran (THF, distilled over lithium aluminum hydride) under nitrogen atmosphere and the reaction mixture is cooled to −78° C. Butyl lithium (1.6 M in hexane) diluted in dry THF (1:1, v:v) is added dropwise and the reaction mixture is stirred for 30 minutes. Thereafter carbon dioxide is bubbled through the reaction mixture for two hours, and afterwards the reaction mixture is allowed to reach room temperature. The THF is evaporated under reduced pressure and the reaction mixture is dissolved in petroleum ether and washed three times with sodium bicarbonate 5%. The water phases are combined, cooled in an ice bath and acidified to pH 1 using 1N HCl, and thereafter extracted with dichloromethane. The organic fraction is separated, dried over magnesium sulfate and filtered, and the solvent is evaporated under reduced pressure to yield α-halo-TMCA typically as a white powder.

The chemical structure of the obtained α-halo-TMCA is verified by spectroscopic methods (NMR, GC-MS), the purity of the product is assessed by TLC and by elemental analysis, and a typical yield of the entire process is about 40%.

Preparation of α-bromo-2,2,3,3-tetramethylcyclopropanecarboxylic acid (α-bromo-TMCA)

α-Bromo-2,2,3,3-tetramethylcyclopropanecarboxylic acid was prepared according to General Procedure 2 presented hereinabove, using bromoform ($CHBr_3$).

$^1$H NMR (300 MHz, $CDCl_3$, TMS): δ=1.24-1.26 (12H) ppm;

MS-EI: m/z (%)=220 (M$^+$);

TLC (dichloromethane:methanol, 96:4) single spot having a retention factor of 0.6;

Chemical analysis for $C_8H_{13}BrO_2$: calculated—C 43.46, H 5.93, Br 36.14; found—C 43.73, H 6.05 Br 36.46; and Melting point: 157-160° C.

Preparation of α-chloro-2,2,3,3-tetramethylcyclopropanecarboxylic acid (α-chloro-TMCA)

α-Chloro-2,2,3,3-tetramethylcyclopropanecarboxylic acid was prepared according to General Procedure 2 presented hereinabove, using chloroform.

$^1$H NMR (300 MHz, $CDCl_3$, TMS): δ=1.24-1.28 (12H) ppm;

MS-EI: m/z (%)=176 (M$^+$);

TLC (dichloromethane:methanol, 96:4) single spot having a retention factor of 0.6;

Chemical analysis for $C_8H_{13}ClO_2$: calculated—C 54.40, H 7.42, Cl 20.07, found—C 54.49, H 7.61, Cl 19.67;

Melting point: 157-159° C.

Preparation of α-fluoro-2,2,3,3-tetramethylcyclopropanecarboxylic acid (α-fluoro-TMCA)

α-Fluoro-2,2,3,3-tetramethylcyclopropanecarboxylic acid was prepared according to the general procedure presented hereinabove, using N-fluorobenzenesulfonimide.

$^1$H NMR (300 MHz, $CDCl_3$, TMS): δ=1.20-1.26 (18H) ppm.

MS-EI: m/z (%)=160 (M$^+$).

TLC (dichloromethane:methanol, 97:3): single spot having a retention factor of 0.4

Chemical analysis for $C_8H_{13}FO_2$: calculated—C59.98, H8.18, F12.04; found—C59.8, H8.01, F12.04.

Melting point: 121-123° C.

Preparation of α-fluoro-2,2,3,3-tetramethylcyclopropanecarboxamide (Compound 1)

Compound 1

α-Fluoro-2,2,3,3-tetramethylcyclopropanecarboxylic acid (α-fluoro-TMCA), was prepared as described hereinabove.

Thionyl chloride (0.085 moles) was dissolved in anhydrous dichloromethane (6 ml) and the solution was added drop-wise at 0° C. to α-fluoro-TMCA (0.056 moles) dissolved in dichloromethane (60 ml). The reaction mixture was stirred overnight and the solvent and excess of thionyl chloride were thereafter removed by distillation under reduced pressure.

The resulting α-fluoro-2,2,3,3-tetramethylcyclopropanecarbonyl chloride was dissolved in dry acetonitrile and slowly added to a stirred and cooled solution of 25% ammonium hydroxide in water:acetonitrile (1:1 v/v). The amidation reaction was monitored by GC-MS, and once the reaction was completed, the organic solvent was evaporated under reduced pressure. The residue was dissolved in ethyl acetate and washed with water, HCl 1N and brine. The organic extracts were dried over magnesium sulfate and filtered, and the solvent was evaporated under reduced pressure. The product was re-crystallized from petroleum ether to afford white crystals having a melting point of 99° C. The overall yield was 76% and the chemical structure of the product was determined by spectroscopic methods (NMR, GC-MS).

$^1$H NMR (300 MHz, $CDCl_3$, TMS): δ=1.277-1.16 (18H), 5.43 (1H) 6.3(1H) ppm.

MS-EI: m/z(%)=159 (M$^+$).

TLC (dichloromethane:methanol, 97:3): single spot having a retention factor of 0.3.

Chemical analysis for C$_8$H$_{14}$FNO: calculated—C60.35, H8.86, N8.80, F11.93; found—C60.34, H8.93, N8.69, F12.14.

Preparation of N-methyl α-fluoro-,2,2,3,3-tetramethylcyclopropanecarboxamide (Compound 2)

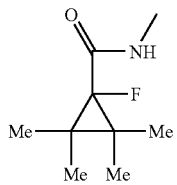

Compound 2

α-Fluoro-2,2,3,3-tetramethylcyclopropanecarbonyl chloride (α-fluoro-TMC-Cl, 0.017 moles), was prepared as described hereinabove, and dissolved in anhydrous dichloromethane, and the dichloromethane solution was added drop-wise to a stirred cooled solution of methyl amine in THF (2 M, 10 ml). The progress of the reaction monitored by GC-MS, and once the reaction was completed the organic solvent was evaporated under reduced pressure and the product was dissolved in ethyl acetate and washed with water, HCl (1N) and brine. The organic fraction was dried over magnesium sulfate, filtered and the solvent was evaporated under reduced pressure.

The product was obtained as a yellowish oil. The overall yield was 94% and the chemical structure of the product was determined by spectroscopic methods (NMR, GC-MS).

$^1$H NMR (300 MHz, CDCl$_3$, TMS): δ=1.07-1.27 (18H), 2.87 (3H) 6.43 (1H) ppm.

MS-EI: m/z (%)=173 (M+).

TLC (dichloromethane:methanol, 97:3): single spot having a retention factor of 0.18.

Chemical analysis for C$_9$H$_{16}$FNO: calculated—C62.40, H9.31, N8.09, F10.97; found—C62.38, H9.48, N7.79, F11.17.

Preparation of α-fluoro-2,2,3,3-tetramethylcyclopropylcarbonylurea (Compound 3)

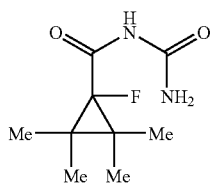

Compound 3

α-Fluoro-2,2,3,3-tetramethylcyclopropanecarbonylchloride (α-fluoro-TMC-Cl, 0.018 moles), was prepared as described hereinabove and dissolved in acetonitrile (7 ml).

Urea (0.045 mole), dissolved in dry acetonitrile (40 ml), was refluxed for one hour and the α-fluoro-TMC-Cl was added thereto drop-wise. The reaction mixture was heated and stirred for two additional hours. The solvent was thereafter evaporated and chloroform (40 ml) was added to the remaining oily residue. The obtained solids were filtered by vacuum using a Buchner funnel, dissolved in ethyl acetate and washed with water. The organic fraction was dried over magnesium sulfate, filtered and evaporated to yield a white powder having a melting point of 232° C. The chemical structure of the product was determined by spectroscopic methods (NMR, GC-MS).

$^1$H NMR (300 MHz, CDCl$_3$, TMS): δ=1.206-1.271 (18H), 5.179 (1H), 8.068-8.293 (2H) ppm.

MS-EI: m/z (%)=202 (M+).

TLC (dichloromethane:methanol, 96:4): single spot having a retention factor of 0.45.

Chemical analysis for C$_9$H$_{15}$FN$_2$O$_2$: calculated—C53.45, H7.48, N13.85, F9.39; found—C53.52, H7.63, N13.74, F9.18.

Preparation of α-alkyl-2,2,3,3-tetramethylcyclopropanecarboxylic acid (α-alkyl-TMCA)—General Procedure A solution of lithiumdiisopropylamine (LDA, 1.1 equivalents) is prepared by dissolving under nitrogen diisopropylamine in THF, freshly distilled over calcium hydride. The reaction mixture is cooled to −15° C. and butyl lithium (BuLi) is added slowly thereto while stirring and maintaining the temperature of the mixture at −15° C. The resulting mixture is then stirred and cooled for additional 10 minutes, and thereafter allowed to warm to 0° C. while stirring for additional 10 minutes. Thereafter the reaction mixture is cooled again to −15° C. and TMCA ethyl ester (1 equivalent), dissolved in dry THF, is added thereto.

After stirring for 40 minutes, in which the temperature of the reaction mixture is elevated to about −8° C., 1.5 equivalents of alkyl iodide dissolved in dry THF are added thereto.

The reaction mixture is stirred while the formation of α-alkyl-TMCA ethyl ester is monitored by GC-MS. Once the reaction is completed the organic solvent is removed under reduced pressure and the typically oily residue is dispersed in ethyl acetate and filtered twice on a Buchner funnel. The solids in the funnel are washed twice with hexane, the hexane and ethyl acetate are combined and washed with water, HCl (1N) and brine, dried over sodium sulfate and filtered.

The α-alkyl-TMCA ethyl ester is hydrolyzed to the corresponding acid using potassium hydroxide (1.5 equivalents) in a water:ethanol mixture.

Preparation of 1,2,2,3,3-pentamethylcyclopropanecarboxamide or α-methyl-2,2,3,3-tetramethylcyclopropanecarboxamide (Compound 4)

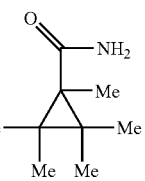

Compound 4

α-methyl-2,2,3,3-tetramethylcyclopropanecarboxylic acid (α-methyl-TMCA), is prepared according to the general procedure described hereinabove, using methyl iodide as the alkylating agent.

Preparation of α-bromo-2,2,3,3-tetramethylcyclopropanecarboxamide (Compound 5)

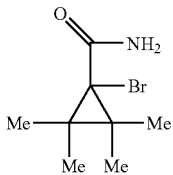

Compound 5

α-Bromo-2,2,3,3-tetramethylcyclopropanecarboxylic acid (α-bromo-TMCA), was prepared as described hereinabove.

Thionyl chloride (0.025 moles) was dissolved in anhydrous dichloromethane (4 ml) and the solution was added drop-wise at 0° C. to α-bromo-TMCA (0.012 moles) dissolved in dichloromethane (10 ml). The reaction mixture was stirred overnight and the solvent and excess of thionyl chloride were thereafter removed by distillation under reduced pressure.

The resulting α-bromo-2,2,3,3-tetramethylcyclopropanecarbonyl chloride was dissolved in dry dichloromethane and slowly added to 20 ml of a stirred and cooled solution of 25% ammonium hydroxide in water:dichloromethane (1:1 v/v). The amidation reaction was monitored by GC-MS, and once the reaction was completed, the organic solvent was evaporated under reduced pressure. The residue was dissolved in ethyl acetate and washed with water, an aqueous solution of 1N HCl and brine. The organic extracts were dried over magnesium sulfate and filtered, and the solvent was evaporated under reduced pressure. The product was re-crystallized from ethyl acetate-petroleum ether to afford white crystals having a melting point of 152° C. The overall yield was 40% and the chemical structure of the product was determined by spectroscopic methods (NMR, GC-MS).

$^1$H NMR (300 MHz, CDCl$_3$, TMS): δ=1.25-1.26 (12H), 5.8-6.3 (2H) ppm;

MS-EI: m/z (%)=219 (M$^+$);

TLC (dichloromethane:methanol, 96:4) single spot having a retention factor of 0.83; and Chemical analysis for C$_8$H$_{14}$BrNO: calculated—C 43.65, H 6.41, N 6.35, Br 36.3; found—C 43.86, H 6.51, N 6.35, Br 36.39.

Preparation of α-chloro-2,2,3,3-tetramethylcyclopropanecarboxamide (Compound 9)

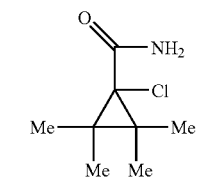

Compound 9

α-chloro-2,2,3,3-tetramethylcyclopropanecarboxylic acid (α-chloro-TMCA), was prepared as described hereinabove.

Thionyl chloride (0.02 moles) was dissolved in anhydrous dichloromethane (4 ml) and the solution was added drop-wise at 0° C. to α-chloro-TMCA (0.01 moles) dissolved in dichloromethane (5 ml). The reaction mixture was stirred overnight.

The resulting α-chloro-2,2,3,3-tetramethylcyclopropanecarbonyl chloride was dissolved in dry dichloromethane and slowly added to 20 ml of a stirred and cooled solution of 25% ammonium hydroxide in water:dichloromethane (1:1 v/v). The amidation reaction was monitored by GC-MS, and once the reaction was completed, the organic solvent was evaporated under reduced pressure. The residue was dissolved in ethyl acetate and washed with water, an aqueous solution of 1N HCl and brine. The organic extracts were dried over magnesium sulfate and filtered, and the solvent was evaporated under reduced pressure. The product was re-crystallized from ethyl acetate to afford white crystals having a melting point of 128° C. The overall yield was 85% and the chemical structure of the product was determined by spectroscopic methods (NMR, GC-MS).

$^1$H NMR (300 MHz, CDCl$_3$, TMS): δ=1.22-1.30 (12H), 5.43-6.23 (2H) ppm;

MS-EI: m/z (%)=175 (M$^+$);

TLC (dichloromethane:methanol, 96:4) single spot having a retention factor of 0.67;

Chemical analysis for C$_8$H$_{14}$BrNO: calculated—C 54.70, H 8.03, N 7.97, Cl 20.18; found—C 54.77, H 8.15, N 7.85, Cl 19.91.

Using the procedures described hereinabove, additional derivatives of α-halo and α-alkyl-2,2,3,3-tetramethylcyclopropanecarboxy compounds are prepared and substituted at the N-amide moiety with different groups such as the TMCA and VPA amide analogues described in, for example, U.S. Pat. Nos. 5,880,157 and 6,960,687, U.S. Patent Applications having Publication Nos. 20050131069, 20060004098 and 20060148861, and M. Bialer et al. in *Pharm. Res.* 13:284-289 (1996), all of which are incorporated herein by reference in their entirety as if fully set forth herein.

Exemplary α-halo and α-alkyl-2,2,3,3-tetramethylcyclopropanecarboxy compounds are presented in Table 1 hereinbelow.

TABLE 1

| Compound type or number | Structure | Name and variables |
|---|---|---|
| Compound according to general Formula I | ![structure] | R$_1$-R$_4$ = alkyl; X = halide or alkyl; Y = NR$_5$, O or S; A = O, N or S; R$_5$ = H, alkyl or D$_2$; D$_1$ = H, alkyl, D$_2$ or absent; D$_2$ = a wide selection of moieties |

| Compound type or number | Structure | Name and variables |
|---|---|---|
| Amide | (cyclopropane with C(=O)NH$_2$, α-X, Me groups) | α-halo or α-alkyl-2,2,3,3-tetramethylcyclopropanecarboxamide<br>$R_1$-$R_4$ = methyl;<br>X = alkyl, F, Cl, Br or I;<br>Y = O;<br>A = N;<br>$D_1$ = $D_2$ = H |
| α-fluoro-Amide | (cyclopropane with C(=O)N($D_2$)$D_1$, α-F, Me groups) | $R_1$-$R_4$ = methyl;<br>X = fluoride;<br>Y = O;<br>A = N;<br>$D_1$ = H, alkyl, $D_2$ or absent;<br>$D_2$ = a wide selection of moieties |
| Compound 1 | (cyclopropane with C(=O)NH$_2$, α-F, Me groups) | α-fluoro-2,2,3,3-tetramethylcyclopropanecarboxamide<br>$R_1$-$R_4$ = methyl;<br>X = fluoro;<br>Y = O;<br>A = N;<br>$D_1$ = $D_2$ = H |
| Compound 4 | (cyclopropane with C(=O)NH$_2$, α-Me, Me groups) | 1,2,2,3,3-pentamethylcyclopropanecarboxamide<br>$R_1$-$R_4$ = methyl;<br>X = methyl;<br>Y = O;<br>A = N;<br>$D_1$ = $D_2$ = H |
| Compound 5 | (cyclopropane with C(=O)NH$_2$, α-Br, Me groups) | α-bromo-2,2,3,3-tetramethylcyclopropanecarboxamide<br>$R_1$-$R_4$ = methyl;<br>X = bromo;<br>Y = O;<br>A = N;<br>$D_1$ = $D_2$ = H |
| Compound 9 | (cyclopropane with C(=O)NH$_2$, α-Cl, Me groups) | α-chloro-2,2,3,3-tetramethylcyclopropanecarboxamide<br>$R_1$-$R_4$ = methyl;<br>X = chloro;<br>Y = O;<br>A = N;<br>$D_1$ = $D_2$ = H |
| N-alkyl amide | (cyclopropane with C(=O)NHMe, α-X, Me groups) | α-halo or α-alkyl-N-methyl-2,2,3,3-tetramethylcyclopropanecarboxamide<br>$R_1$-$R_4$ = methyl;<br>X = alkyl, F, Cl, Br or I;<br>Y = O;<br>A = N;<br>$D_1$ = H;<br>$D_2$ = methyl |
| Compound 2 | (cyclopropane with C(=O)NHMe, α-F, Me groups) | α-fluoro-N-methyl-2,2,3,3-tetramethylcyclopropanecarboxamide<br>$R_1$-$R_4$ = methyl;<br>X = fluoro;<br>Y = O;<br>A = N;<br>$D_1$ = H;<br>$D_2$ = methyl |

TABLE 1-continued

| Compound type or number | Structure | Name and variables |
|---|---|---|
| N-methoxy amide | (structure) | α-halo or α-alkyl-N-methyl-2,2,3,3-tetramethylcyclopropanecarboxamide<br>$R_1$-$R_4$ = methyl;<br>X = alkyl, F, Cl, Br or I;<br>Y = O;<br>A = N;<br>$D_1$ = H;<br>$D_2$ = methyl |
| Compound 8 | (structure) | α-fluoro-N-methoxy-2,2,3,3-tetramethylcyclopropanecarboxamide<br>$R_1$-$R_4$ = methyl;<br>X = fluoro;<br>Y = O;<br>A = N;<br>$D_1$ = H;<br>$D_2$ = methoxy |
| Compound according to general Formula I and Formula IX | (structure) | $R_1$-$R_4$ = methyl;<br>X = alkyl, F, Cl, Br or I;<br>Y = O;<br>A = N;<br>$D_1$ = H;<br>$D_2$ = —C(=O)—$(CH_2)_n$—$NR_6R_7$;<br>n = 0, 1, 2, ..., n<br>$R_6$, $R_7$ = H, alkyl or a wide selection of moieties; |
| carbonyl urea | (structure) | α-halo or α-alkyl-2,2,3,3-tetramethylcyclopropylcarbonyl urea<br>$R_1$-$R_4$ = methyl;<br>X = alkyl, F, Cl, Br or I;<br>Y = O;<br>A = N;<br>$D_1$ = H;<br>$D_2$ = —C(=O)—$(CH_2)_n$—$NR_6R_7$;<br>n = 0<br>$R_6$, $R_7$ = H |
| Compound 3 | (structure) | α-fluoro-2,2,3,3-tetramethylcyclopropylcarbonyl urea<br>$R_1$-$R_4$ = methyl;<br>X = fluoro;<br>Y = O;<br>A = N;<br>$D_1$ = H;<br>$D_2$ = formamide or carbonyl amide |
| N-(1,3,4-thiadiazole-2-sulfonamide) amide | (structure) | α-halo or α-alkyl-N-(1,3,4-thiadiazole-2-sulfonamide)-2,2,3,3-tetramethylcyclopropanecarboxamide<br>$R_1$-$R_4$ = methyl;<br>X = alkyl, F, Cl, Br or I;<br>Y = O;<br>A = N;<br>$D_1$ = H;<br>$D_2$ = [1,3,4]thiadiazole-2-sulfonic acid amide |
| Compound 6 | (structure) | α-fluoro-2,2,3,3-tetramethyl-cyclopropanecarboxylic acid (5-sulfamoyl-[1,3,4]thiadiazol-2-yl)-amide<br>$R_1$-$R_4$ = methyl;<br>X = fluoro;<br>Y = O;<br>A = N;<br>$D_1$ = H;<br>$D_2$ = [1,3,4]thiadiazole-2-sulfonic acid amide |

TABLE 1-continued

| Compound type or number | Structure | Name and variables |
|---|---|---|
| Compound according to general Formula I and Formula X N-(3-alkyl-5-sulfamoyl-1,3,4-thiadiazol-2(3H)-ylidene) amide | [structure] | α-halo or α-alkyl-2,2,3,3-tetramethyl-N-(3-alkyl-5-sulfamoyl-1,3,4-thiadiazol-2(3H)-ylidene)cyclopropanecarboxamide $R_1$-$R_4$ = methyl; $R_8$ = alkyl X = alkyl, F, Cl, Br or I; Y = O; A = N; $D_2$ = 3-alkyl-4,5-dihydro-[1,3,4]thiadiazole-2-sulfonic acid amide |
| Compound 7 | [structure] | α-fluoro-2,2,3,3-tetramethyl-N-(3-methyl-5-sulfamoyl-1,3,4-thiadiazol-2(3H)-ylidene)cyclopropanecarboxamide $R_1$-$R_4$ = methyl; $R_8$ = methyl; X = fluoro; Y = O; A = N; $D_2$ = 3-methyl-4,5-dihydro-[1,3,4]thiadiazole-2-sulfonic acid amide |

Example 2

In-Vivo Activity

Anticonvulsant Activity Assays:

The α-halo-2,2,3,3-tetramethylcyclopropanecarboxy compounds of the present embodiments were tested for their ability to protect against chemically and electrically induced convulsions, in several models of epilepsy in mice and rats.

In the first model, the maximal electroshock seizure test (MES) was used to show efficacy for antiepileptic agents against partial and generalized seizure type epilepsy, the common epilepsy among therapy resistant epileptic patients. In the second model, the subcutaneous metrazol test (scMet) was used to measure seizure threshold and was used as a standard screening procedure to show efficacy for agents against seizure threshold and absence seizures.

The models and the biological activity protocols followed in the examples presented herein have been described in the art [27].

Briefly, Maximal Electroshock Seizure (MES) assay measures drug capacity to prevent seizure spread and is thus considered to model generalized tonic-clonic seizures. The assay was conducted using a supra-maximal current of 50 mA and 60 Hz for 0.2 seconds in mice, and 150 mA and 60 Hz for 0.2 seconds in rats. The current was delivered to the subjects by means of corneal electrodes to produce tonic hind limb extension. Animals not displaying tonic hind limb extension were considered affected positively by the tested compound.

Subcutaneous Metrazole Seizure Threshold Test (scMet) assay measures the ability of an agent to elevate seizure threshold and is considered to model generalized absence seizures. The assay was performed by subcutaneous injection of 85 mg/kg of the convulsant agent metrazole that induces clonic seizures in at least 97% of all animal models (rats and mice).

In a third model, the hippocampal kindling assay [27, 28] was used to identify new drug candidates effective for the treatment of difficult-to-control seizure types, focal seizures and complex partial seizures, as well as compounds that may be effective as mood stabilizer for treating bipolar disorder [28], and was conducted according to the protocol described therein.

Briefly, this test was conducted by using a bipolar stimulating electrode which was implanted in the hippocampus of rats, and the rats were kindled according to a described method [29]. One week after implantation of the electrodes, the rats were stimulated with supra-threshold trains of 200 μA and 50 Hz for 10 seconds every 30 minutes for 6 hours on alternate days until the animals were fully kindled. Animals were considered fully kindled when they displayed stable stage 5 seizures. The behavioral seizures were scored according to the following criteria ("seizure score"): stage 1—mouth and facial clonus; stage 2—stage 1 plus head nodding; stage 3—stage 2 plus forelimb clonus; stage 4—stage 3 plus rearing; and stage 5—stage 4 plus repeated rearing and falling.

In a fourth model, the compounds were tested for their ability to block 6 Hz (32 mA) seizures following intraperitoneal administration thereof to male mice. This test is used to measure the effectiveness of new drug candidates against tonic-clonic seizures and generalized myoclonic seizures and is considered a model for therapy resistance for the treatment of therapy-resistant partial seizures.

Briefly, psychomotor seizure (6-Hz) assay measures the resistance of a subject to induced psychomotor seizures. The assay was conducted in mice which were pretreated with the test compound. At varying times after treatment, individual subjects were challenged with sufficient current of 32 mA at 6 Hz for 3 seconds, or 44 mA at 6 Hz for 3 seconds, delivered through corneal electrodes to elicit a psychomotor seizure. Animals which were not affected by the current were considered affected positively by the tested compound, thus compounds which were found active in this test are considered promising novel drug candidates for the treatment of therapy-resistant seizures.

In a fifth model, the pilocarpine model of epilepsy was used to measure seizure threshold and was used as a standard screening procedure to show efficacy of the compounds presented herein against Status Epilepricus (SE) seizures. The models and the biological activity protocols followed in the examples presented herein have been described in the art [30]. This model shares many characteristics with nerve agent induced seizures since both initiation and early expression of nerve agent induced seizures are cholinergic followed by the recruitment of other neurotransmitter systems that serve to reinforce recurring seizure activity progressing to Status Epilepricus.

Briefly, the Pilocarpine Induced Epilepsy model (PIE) consists of systemic administration of the cholinergic agent and muscarinic agonist pilocarpine which induces spontaneous seizures in subjects after a latency of 14-15 days. Experiments presented in the art demonstrated that structural damage of the brain leads to spontaneous recurrent seizures. The characteristic of the seizure resembles human partial epilepsy. In rats, a behavior (akinesia, facial automatisms, limbic seizures consisting of forelimb clonus with rearing, salivation, masticatory jaw movements, and falling) and EEG changes (significant theta rhythm and isolated spikes in hippocampus, synchronization of the activity in hippocampus and cortex, EEG seizures, status epilepticus) can be observed and recorded.

The application of this model in rodents causes the induction of both fetal arid interictal activity in hippocampal and cortical regions of the brain. Clinical manifestations include ataxia, akinesia and facial automatisms where symptoms quickly progress to full SE lasting up to twelve hours. This protective activity can be correlated closely with electrographic changes, depending of the level of protection observed in the initial qualitative screen a series of evaluations using this chemoconvulsant may be employed to assess certain pharmacological characteristics of candidate compounds. Specifically, the effects of systematic administration of pilocarpine in rats promotes sequential behavioral and electrographic changes that can be divided in three distinct periods: (a) an acute period that built up progressively into a limbic status epilepticus and that lasts 24 hours, (b) a silent period with a progressive normalization of EEG and behavior which varies from 4 to 44 days, and (c) a chronic period with spontaneous recurrent seizures (SRSs). The main features of the SRSs observed during the long-term period resemble those of human complex partial seizures and recurs 2-3 times per week per animal. Therefore, this experimental approach serves as a model of epilepsy mimicking the human condition.

Results of Anticonvulsant Activity Assays:

The median effective dose ($ED_{50}$) is the dose of a drug predicted by statistical techniques to produce a characteristic effect in 50 percent of the subjects to whom the dose is given. The $ED_{50}$ of α-Fluoro-2,2,3,3-tetramethylcyclopropanecarboxamide (Compound 1), presenting the anticonvulsant activity of this compound, was determined in the rat scMet, hippocampal kindling, pilocarpin SE and in the 6 Hz models in mice (32 mA, 44 mA), by administering various doses thereof and measuring the fractions of animals which responded to the treatment. Table 2 presents the experimental results obtained in the scMet rat models, according to which the $ED_{50}$ of Compound 1 was evaluated.

TABLE 2

| Dose (mg/kg) | Fraction of rats which responded to the treatment |
|---|---|
| 2 | 0/8 |
| 6 | 5/8 |
| 12.5 | 6/8 |
| 25 | 8/8 |

As shown in Table 2, following oral administration to rats, the $ED_{50}$ of Compound 1 was evaluated as 6 mg/kg with a 95% confidence interval (CI) of 3.6 to 9.5 mg/kg.

For comparison, 2,2,3,3-tetramethylcyclopropanecarbonyl urea (TMC-Urea) exhibited an $ED_{50}$ of 92 mg/kg with a 95% confidence interval (CI) of 50-151 mg/kg as measured in rat scMet models [13], and N-2,2,3,3-tetramethylcyclopropylcarbonyl-glycinamide was found inactive at a dose of 250 mg/kg ($ED_{50}$ greater than 250 mg/kg) [Bialer et al., *Pharm. Res.* 13 (2):284-289, 1996].

Table 3 presents the calculated $ED_{50}$ of Compound 1 obtained in the various rat and mice models.

TABLE 3

| Test | $ED_{50}$ (mg/kg) | $ED_{50}$ (mmol/kg) | Toxicity ($TD_{50}$ mg/kg) |
|---|---|---|---|
| ScMet (rats, p.o.) | 6 (3.5-9.5) | 0.04 (0.02-0.06) | 117 |
| Hippocampal kindled (rats) | 29.52 (16.8-53.0) | 0.18 | — |
| 6 Hz 44 mA (mice) | ~50 | ~0.31 | Minimal motor impairment |
| 6 Hz 32 mA (mine) | <50 | <0.31 | — |
| Pilocarpine induced SE (rats, 30 minutes) | 79.9 (50-100) | 0.5 | — |

Table 4 presents the anticonvulsant activity of α-methyl-2,2,3,3-tetramethylcyclopropanecarboxamide (Compound 4) was tested in the rat MES and scMet models. The $ED_{50}$ of Compound 4 was not determined quantitatively, but was estimated to be lower than 50 mg/kg.

TABLE 4

| Test | Dose (mg/kg) | Time after dosing (hours) | | | | |
|---|---|---|---|---|---|---|
| | | 0.25 | 0.5 | 1.0 | 2.0 | 4.0 |
| MES (rat p.o) | 50 | 0/4 | 0/4 | 0/4 | 0/4 | 0/4 |
| ScMet (rat p.o.) | 50 | 0/4 | 0/4 | 1/4 | 1/4 | 0/4 |
| Toxicity (rat p.o) | 50 | 0/4 | 0/4 | 0/4 | 0/4 | 0/4 |

Neurotoxicity Assays:

Neurotoxicity assays are design to assess the effect of putative neurotoxicants on the normal activity of the nervous system, which can adversely disrupt or cause neuronal death, and damage other parts of the nervous system. The median neurological toxic dose ($TD_{50}$) is used for quantization of neurotoxicity.

The neurotixicity studies were conducted according to the protocol described in White, H. S., et al., in "General principles. Discovery and preclinical development of antiepileptic drugs", 5th edition, Levy R H, Mattson R H, Meldrum B S, Perucca E. (editors); *Antiepileptic drugs*; Lippincott-Raven; Philadelphia: 2002. pp. 36-48.

Neurotoxicity of the α-halo-2,2,3,3-tetramethylcyclopropanecarboxy compounds of the present embodiments was assessed in rats treated therewith by oral administration and observed in the "gait and stance" assay, which assesses minimal neurotoxicity. The neurotoxicity studies were conducted according to the protocol described in White H S. et al., General principles-Discovery and preclinical development of antiepileptic drugs, in: Antiepileptic Drugs, 5th edition, R H Wilkins, Philadelphia 2002, pp. 36-48.

Results of Neurotoxicity Assays:

The protective index (PI) is defined as the ratio of $TD_{50}$ and $ED_{50}$ (PI=$TD_{50}/ED_{50}$). The PI is used to show a beneficial segregation between neurotoxicity and antiepileptic activity, and can therefore be regarded as the margin of safety, namely the higher the PI the better is the pharmaceutical profile in terms of neurotoxicity and the efficacious doses.

The $TD_{50}$ of Compound 1 following oral administration to rats was found to be 117 mg/kg.

For comparison, the $TD_{50}$ of TMC-Urea is 538 mg/kg following oral administration to rats, and N-methyl-2,2,3,3-tetramethylcyclopropanecarboxamide has a $TD_{50}$ of 163 mg/kg (CI=138-179 mg/kg) [N. Isoherranen et al, Epilepsy, 43(2): 115-126, 2002]. VPA exhibits a $TD_{50}$ value of 280 mg/kg and 2,2,3,3-tetramethylcyclopropylcarbonyl-glycinamide exhibits a $TD_{50}$ of above 500 mg/kg [Bialer et al., Pharm. Res. 13 (2):284-289, 1996].

Thus, the protective index ($TD_{50}/ED_{50}$) is 2 for N-methyl-2,2,3,3-tetramethylcyclopropanecarboxamide, 0.6 for VPA, higher than 6.1 for 2,2,3,3-tetramethylcyclopropylcarbonyl-glycinamide, 18.5 for TMC-urea and 19.5 for α-fluoro-2,2,3,3-tetramethylcyclopropanecarboxamide (Compound 1).

These results clearly indicate that α-fluoro-2,2,3,3-tetramethylcyclopropane carboxamide (Compound 1), an exemplary novel compound according to the present embodiments, has a great potential as a drug for the treatment of epilepsy.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED BY NUMERALS

Other References are Cited in the Text

[1] R. H. Levy, D. D. Shen, F. S. Abbott, W. Riggs and H. Hachad. Valproic acid: Chemistry, biotransformation and pharmacokinetics. In: Antiepileptic Drugs, 5th edition, R. H. Levy, R. H. Mattson, B. S. Meldrum and E. Perucca (eds), Lippincott, Philadelphia, 2002, pp. 780-800 and other chapters on valproic acid therein.

[2] R. Jensen, T. Brinck and J. Olesen. Sodium valproate has a prophylactic effect in migraine without aura: a triple blind, placebo-controlled crossover study. Neurology 44:647-651 (1994).

[3] H. McQuay, D. Carrol, A. R. Jadad, P. Wiffen and A. Moore. Anticonvulsant drugs for the management of pain: a systematic review. Brit. Med. J. 311:1047-1052 (1995).

[4] T. de Paulis. ONO-2506. Curr. Opin. Investig. Drug. 4:863-867 (2003).

[5] W. Loscher. Basic pharmacology of valproate: a review after 35 years of clinical use for the treatment of epilepsy. CNS Drugs. 16:669-694 (2002).

[6] W. Loscher. Valproate: a reappraisal of its pharmacodynamic properties and mechanisms of action. Prog Neurobiol 58:31-59 (1999).

[7] M. J. Owens and C. B. Nemeroff. Pharmacology of valproate. Psychopharmacol Bull. 37 Suppl 2:17-24 (2003).

[8] H. Nau. Valproic acid teratogenesis in mice after various administration and phenobarbital-pretreatment regimens: The parent drug and not one of the metabolites assayed is implicated as teratogen. Fund Appl Toxicol 6:662-668 (1986).

[9] T. A. Baillie, P. R. Scheffels. Valproic acid, chemistry and biotransformation. In: R. H. Levy, R. H. Mattson, B. S. Meldrum, eds. Antiepileptic Drugs. 4th edition, New York: Raven Press, 1995, pp. 589-603.

[10] N. Isoherranen, S. H. White, R. H. Finnell, B. Yagen, J. H. Woodhead, G. D. Bennet, K. S. Wilcox, M. E. Barton and M. Bialer. Anticonvulsant profile and teratogenicity of N-methyl-tetramethylcyclopropyl carboxamide: a new antiepileptic drug. Epilepsia 43: 115-126 (2002).

[11] N. Isoherranen, B. Yagen and M. Bialer. New CNS-active drugs which are second-generation valproic acid: can they lead to the development of a magic bullet? Curr Opin Neurol 16:203-11 (2003).

[12] N. Isoherranen, R. H. Levy, B. Yagen, J. H. Woodhead, H. S. White and M. Bialer. Metabolism of a new antiepileptic drug, N-methyl cyclopropane carboxamide, and anticonvulsant activity of its metabolites. Epilepsy Res 58:1-12 (2004).

[13] E. Sobol, M. Bialer and B. Yagen. Tetramethylcyclopropyl analogue of a leading antiepileptic drug, valproic acid. Synthesis and evaluation of anticonvulsant activity of its amide derivatives. J Med Chem 47:4316-4326 (2004).

[14] I. Winkler, E. Sobol, B. Yagen, A. Steinman, M. Devor and M. Bialer. Efficacy of antiepileptic tetramethylcyclopropyl analogs of valproic acid amides in a rat model for neuropathic pain. Neuropharmacology 49:1110-1120 (2005).

[15] I. Winkler, S. Blotnik, J. Shimshoni, B. Yagen, M. Devor and M. Bialer. Efficacy of antiepileptic isomers of valproic acid valpromide in a rat model for neuropathic pain. Brit J Pharmacol 146:198-208 (2005).

[16] G. Shaltiel, A. Shamir, J. Shapiro, D. Ding, E. Dalton, M. Bialer, A. J. Harwood, R. H. Belmaker, M. L. Greenberg and G. Agam. Valproate decreases inositol biosynthesis. Biol. Psychiatr. 56:868-874 (2004).

[17] J. Shimshoni, E. C. Dalton, A. Jenkins, S. Eyal, K. Ewen, R. S. B. Williams, B. Yagen, J. A. Harwood and M. Bialer. Probing CNS-active analogues and amide derivatives of valproic acid for mood stabilizer properties. Submitted to Neuropsychopharmacology.

[18] W. Tang, J. Palady and F. J. Abbott. Time course of α-fluorinated valproic acid in mouse brain and serum and its effect of synaptosomal γ-aminobutyric acid levels in comparison to valproic acid. J. Pharmacol Exp Ther 282: 1163-1172 (1997).

[19] D. Eikel, A. Lapman and H. Nau. Histonedeacetylases are new molecular targets whose inhibition can cause birth defects: evidence from structure-activity relationship study of valproic acid derivatives. Reprod Toxicol 18:723-724 (2004).

[20] N. Isoherranen, B. Yagen, S. Blotnik, O. Spiegelstein, K. S. Wilcox, J. H. Woodhead, R. H. Finnell, H. S. White and M. Bialer. Characterization of the anticonvulsant activity and pharmacokinetics of propylisopropyl acetamide and its enantiomers. Br J Pharmacol 138:602-613 (2003).

[21] N. Isoherranen, H. S. White, B. D. Klein, M. Roeder, B. Yagen, J. H. Woodhead, V. Schurig and M. Bialer. Pharmacokinetic-pharmacodynamic relationships of 2S,3S-valnoctamide and its stereoisomer 2R,3S-valnoctamide in animal models for epilepsy. Pharm Res 20:1293-1301 (2003).
[22] M. Bialer, S. J. Johannessen, H. J. Kupferberg, R. H. Levy, E. Perucca and T. Tomson. Progress report on new antiepileptic drugs: A summary of the Seventh Eilat Conference (EILAT VII). Epilepsy Res. 61:1-48 (2004).
[23] M. Britzi, S. Soback, N. Isoherranen, R. H. Levy, E. Perucca, D. R. Doose, B. E. Maryanoff and M. Bialer. Analysis of topiramate and its metabolites in plasma and urine of healthy subjects and patients with epilepsy by use of a novel liquid chromatography-mass spectrometry assay. Ther Drug Monit. 25: 314-322 (2003).
[24] M. Britzi, E. Perucca, S. Soback, R. H. Levy, C. Fattroe, F. Crema, G. Gatti, D. R. Doose, B. E. Maryanoff and M. Bialer. Pharmacokinetic and metabolic investigation of topiramate disposition in healthy subjects in presence and absence of enzyme induction by carbamazepine. Epilepsia 46:378-384 (2005).
[25] D. Mimrod, L. M. Specchio, M. Britzi, E. Perucca, N. Specchio, A. La Neve, S. Soback, R. H. Levy, G. Gatti, D. R. Doose, B. E. Maryanoff and M. Bialer. A comparative study of the effect of carbamazepine and valproic acid on the pharmacokinetics and metabolic profile of topiramate at steady-state in patients with epilepsy. Epilepsia 46:1-46-1065 (2005).
[26] E. Sobol, B. Yagen, I. Winkler, M. Britzi, D. Gibson and M. Bialer. Pharmacokinetics and metabolism of a new potent anticonvulsant agent, 2,2,3,3-tetramethylcyclopropylcarbonylurea in rats. Drug Metab. Disposit. 33;1538-1546 (2005).
[27] White, H. S., ed. General principles. Discovery and preclinical development of antiepileptic drugs. 5 ed. Antiepileptic drugs, ed. M. R. Levy R H, Meldrum B S, Perucca E. 2002, Lippincott-Raven: Philadelphia. 36-48.
[28] Weiss, S. R. and R. M. Post, Kindling: separate vs. shared mechanisms in affective disorders and epilepsy. Neuropsychobiology, 1998. 38(3): p. 167-80.
[29] Lothman, E. W., et al., *Screening and characterization of antiepileptic drugs with rapidly recurring hippocampal seizures in rats*. Epilepsy Res, 1988. 2(6): p. 367-79.
[30] Cavalheiro, E. A., The pilocarpine model of epilepsy. The Italian Journal of Neurological Sciences, 1995. 16(1-2): p. 33-37.

What is claimed is:
1. A pharmaceutical composition comprising, as an active ingredient, a compound having the general Formula:

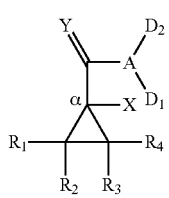

Formula I an enantiomer, a prodrug, a hydrate, a solvate or a pharmaceutically acceptable salt thereof and a pharmaceutically acceptable carrier;
wherein:
X is halide;
$R_1$-$R_4$ are each independently an alkyl having from 1 to 20 carbon atoms;
Y is selected from the group consisting of $NR_5$, O and S;
A is selected from the group consisting of O, N and S;

$R_5$ is selected from the group consisting of hydrogen, alkyl and cycloalkyl; and
$D_1$ and $D_2$ are each independently selected from the group consisting of hydrogen, alkyl, alkenyl, alkynyl, cycloalkyl, aryl, heteroaryl, halide, hydroxy, alkoxy, hydroxyalkyl, thiohydroxy, thioalkoxy, thiohydroxyalkyl, aryloxy, thioaryloxy, haloalkyl, amine, carbonyl, amide, thioamide, carbamate, alkyl-sulfonamide, arylsulfonamide, alkyl-aryl-sulfonamide, thiadiazole-sulfonamide, alkyl-thiadiazole-sulfonamide or absent, the pharmaceutical composition being formulated for administration.
2. The pharmaceutical composition of claim 1, being packaged in a packaging material and identified in print, in or on said packaging material, for use in substantially inhibiting, slowing the progression of, or substantially ameliorating clinical or aesthetical symptoms of a neurological disease or disorder, said neurological disease or disorder being selected from the group consisting of epilepsy, convulsions, seizure disorders, status epilepticus, a chemically-induced convulsion and/or seizure disorder, a febrile convulsion condition, a metabolic disturbance, a sustenance withdrawal condition, spasticity, skeletal muscle spasms, restless leg syndrome, anxiety, stress, multiple sclerosis, stroke, head trauma, spinal cord injury, amytrophic lateral sclerosis (ALS), Parkinson's Disease, Huntington's Disease, Alzheimer's Disease, amyotrophic lateral sclerosis, neuropathic pain, deafferentation pain, myoclonus, schizophrenia, migraine, headaches and bipolar disorder.
3. The pharmaceutical composition of claim 2, wherein said neurological disease or disorder is epilepsy.
4. The pharmaceutical composition of claim 1, wherein X is fluoro.
5. The pharmaceutical composition of claim 1, wherein each of $R_1$-$R_4$ is methyl.
6. The pharmaceutical composition of claim 1, wherein Y is O.
7. The pharmaceutical composition of claim 1, wherein A is N.
8. The pharmaceutical composition of claim 1, wherein each of $D_1$ and $D_2$ is hydrogen.
9. The pharmaceutical composition of claim 1, wherein:
X is fluoro;
each of $R_1$-$R_4$ is methyl;
Y is O;
A is N; and
each of $D_1$ and $D_2$ is hydrogen.
10. The pharmaceutical composition of claim 1, being formulated for oral administration.
11. The pharmaceutical composition of claim 10, being in the form selected from the group consisting of a powder, a plurality of granules, a suspension, an aqueous solution, a non-aqueous solution, a pill, a caplet, a capsule and a tablet.
12. A method of substantially inhibiting, slowing the progression of, or substantially ameliorating clinical or aesthetical symptoms of a neurological disease or disorder, the neurological disease or disorder being selected from the group consisting of epilepsy, convulsions, seizure disorders, status epilepticus, a chemically-induced convulsion and/or seizure disorder, a febrile convulsion condition, hypoglycemia, hyponatremia, hypoxia, a substance withdrawal condition, spasticity, skeletal muscle spasms, restless leg syndrome, anxiety, stress, multiple sclerosis, stroke, head trauma, spinal cord injury, amytrophic lateral sclerosis (ALS), Parkinson's Disease, Huntington's Disease, Alzheimer's Disease, amyotrophic lateral sclerosis, neuropathic pain, deafferentation pain, myoclonus, schizophrenia, migraine, headaches and bipolar disorder, the method comprising administering to a subject in need thereof a therapeutically effective amount of a compound having the general Formula I:

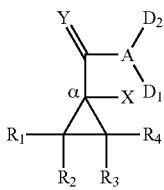

Formula I an enantiomer, a prodrug, a hydrate, a solvate or a pharmaceutically acceptable salt thereof and a pharmaceutically acceptable carrier;
wherein:
X is halide;
$R_1$-$R_4$ are each independently an alkyl having from 1 to 20 carbon atoms;
Y is selected from the group consisting of $NR_5$, O and S;
A is selected from the group consisting of O, N and S;
$R_5$ is selected from the group consisting of hydrogen, alkyl and cycloalkyl; and
$D_1$ and $D_2$ are each independently selected from the group consisting of hydrogen, alkyl, alkenyl, alkynyl, cycloalkyl, aryl, heteroaryl, halide, hydroxy, alkoxy, hydroxyalkyl, thiohydroxy, thioalkoxy, thiohydroxyalkyl, aryloxy, thioaryloxy, haloalkyl, amine, carbonyl, amide, thioamide, carbamate, alkyl-sulfonamide, aryl-sulfonamide, alkyl-aryl-sulfonamide, thiadiazole-sulfonamide, alkyl-thiadiazole-sulfonamide or absent.

13. The method of claim 12, wherein said disease or disorder is epilepsy.

14. The method of claim 12, wherein said therapeutically effective amount ranges from about 0.1 mg/kg body to about 100 mg/kg body.

* * * * *